(12) United States Patent
Nicolson et al.

(10) Patent No.: US 10,307,071 B2
(45) Date of Patent: Jun. 4, 2019

(54) ECG EVALUATION

(71) Applicant: University of Leicester, Leicester, Leicestershire (GB)

(72) Inventors: William B. Nicolson, Leicester (GB); Andre G. Ng, Leicester (GB)

(73) Assignee: University of Leicester, Leicester, Leicestershire (GB)

( * ) Notice: Subject to any disclaimer, the term of this patent is extended or adjusted under 35 U.S.C. 154(b) by 0 days.

(21) Appl. No.: 15/300,684

(22) PCT Filed: Apr. 2, 2015

(86) PCT No.: PCT/GB2015/051049
§ 371 (c)(1),
(2) Date: Sep. 29, 2016

(87) PCT Pub. No.: WO2015/150831
PCT Pub. Date: Oct. 8, 2015

(65) Prior Publication Data
US 2017/0112402 A1    Apr. 27, 2017

(30) Foreign Application Priority Data
Apr. 4, 2014 (GB) .................................. 1406137.8

(51) Int. Cl.
| | | |
|---|---|---|
| A61B 5/0452 | (2006.01) | |
| A61B 5/04 | (2006.01) | |
| G16H 50/30 | (2018.01) | |
| A61B 5/0408 | (2006.01) | |
| A61B 5/00 | (2006.01) | |
| G06F 19/00 | (2018.01) | |
| A61B 5/024 | (2006.01) | |
| A61B 5/0464 | (2006.01) | |

(52) U.S. Cl.
CPC ........ *A61B 5/04012* (2013.01); *A61B 5/0452* (2013.01); *A61B 5/04085* (2013.01); *A61B 5/7275* (2013.01); *G06F 19/00* (2013.01); *G16H 50/30* (2018.01); *A61B 5/02405* (2013.01); *A61B 5/0464* (2013.01)

(58) Field of Classification Search
CPC .................... A61B 5/04012; A61B 5/0452
See application file for complete search history.

(56) References Cited

U.S. PATENT DOCUMENTS

2013/0245474 A1* 9/2013 Nicolson .............. A61B 5/0464
600/518

* cited by examiner

*Primary Examiner* — Rex R Holmes
(74) *Attorney, Agent, or Firm* — Shook, Hardy & Bacon L.L.P.

(57) ABSTRACT

A method for assessing the electrical function of a heart, a method for determining a subject's need for the implantation of an implantable cardioverter defibrillator or the need for administration of an anti-arrhythmic agent, and apparatus for assessing the function of the heart and a computer program product. The methods and products involve analysis of ECG.

23 Claims, 23 Drawing Sheets

ECG EVALUATION

The present invention relates to a method for evaluating cardiac function, in particular a method that utilises the information provided by electrocardiography. The invention also relates to an apparatus in which the aforementioned method may be practised, including a computer program.

The intrinsic conducting system of the heart permits electrical impulses originating from the sinoatrial node to travel through the cardiac tissue in a controlled manner. The passage of this electrical impulse through the heart tissue produces a wave of contraction through the cardiac tissue. The wave of contraction is followed by a period of relative electrical calm in the heart tissue, which corresponds to relaxation of the cardiac tissue. Arrhythmias occur when this normal, organised electrical activity of the heart becomes disrupted. Worldwide 3 million people a year die from sudden cardiac death. In most cases there is no warning and the heart is stopped by a sudden arrhythmia. Some people are at high risk of sudden cardiac death, but this can be prevented by an implantable cardioverter defibrillator, which is implanted in a minor operation.

In the UK, subjects are screened for risk of sudden cardiac death using the National Institute for Health and Clinical Excellence (NICE) guidelines (a screening that is based on a mixture of physiological and electro-physiological measurements and an understanding of the subject's clinical history). However, most of the people who die from sudden cardiac death are not identified by these guidelines.

Assessment of the health of the heart by measuring its electrical activity is known. For example, one can measure the electrical activity of the heart with the use of intra-cardiac electrodes that are directly applied to the cardiac tissue. This is however a particularly invasive technique that is not preferable for the routine assessment of subjects and that has not been clearly shown to demonstrate any clinical relevance for assessing cardiac function such as the risk of arrhythmia. Electrocardiography (ECG) has been developed as a non-invasive procedure for studying the electrical activity of the heart. ECG involves the placing of a plurality of electrodes on the skin surface of a subject. An understanding of the electrical activity of the heart may be identified from the potential difference (i.e. leads) between combinations of the plurality of electrodes. Conventionally, a collective assessment of ECG leads provide a classic ECG tracing, which comprises a P wave, a QRS complex and a T wave, and which demonstrate periods of electrical activity that vary from the isoelectric line. It has been suggested that ECGs may be useful for identifying arrhythmia of the heart by measuring the dispersion of QT durations on an ECG tracing. Measuring changes in this QT duration as an indicator of cardiac arrhythmia has however since been discredited; to the degree that the cardiology community no longer view the QT dispersion assessment as a clinically relevant way to establish arrhythmia risk (see, for example, Malik et al.; JACC; 2000; 36:1749-66).

The present inventors have identified a further means of analysis of ECG output that has proved useful in evaluating cardiac function. The analysis, termed "Regional Restitution Instability Index or R2I2", essentially evaluates the between lead differences in ECG output as an indicator of cardiac function (see International Patent Publication No. WO 2011/117608 A1 and Nicolson et al. "A Novel Surface Electrocardiogram-Based Marker of Ventricular Arrhythmia Risk in Patients with Ischemic Cariomyopathy" J. American Heart Association, 2012).

There however remains a need for further methods and apparatus capable of identifying the risk of sudden cardiac death due to arrhythmia. Such methods and apparatus would be particularly useful for identifying those individuals who are most likely to benefit from the implantation of an implantable cardioverter defibrillator or from treatment with anti-arrhythmic therapeutics.

It has surprisingly been found by the present inventors that analysis of the change in relationship between action potential duration and the diastolic interval taken over multiple time periods by each lead of an ECG presents result that can indicate whether or not an individual being analysed is likely to go on to develop an arrhythmia.

Accordingly, in the first aspect of the present invention, there is provided a method for assessing the electrical function of a heart, comprising the steps of: — a. for each of a plurality of leads of an ECG, at multiple time points, determining a value derived from the output of that lead and which corresponds to an action potential duration;

b. for each of the plurality of leads of the ECG, at the multiple time points, determining a value derived from the output of that lead and which corresponds to a diastolic interval;

c. for each of the plurality of leads of the ECG, using the determined values for action potential duration and diastolic interval across the multiple time points to determine a relationship between action potential duration and diastolic interval as seen by that lead;

d. defining at least one characteristic of interest of each of the determined relationships between action potential duration and diastolic interval and combining information on that characteristic from the relationships seen by the plurality of leads to derive a combined value;

e. deriving an assessment result by analysing the combined value.

An ECG provides a cutaneous electrocardiagraphic measurement of the electrical functioning of the heart. As would be known to the skilled person, an ECG includes a plurality of electrodes that are placed on specific external positions of the body. A lead of an ECG is the potential difference between two or more of these electrodes. Consequently, a lead provides an electrical output that corresponds to a changing potential difference between the electrodes that form the lead.

The plurality of leads available in an ECG would be known to the skilled person (see, for example, "The ECG made easy", 4th edition, John R. Hampton, Churchill Livingstone, 1997). For example, the leads may comprise or consist: limb leads, chest leads, posterior leads, anterior leads, lateral leads, inferior leads, or any combination thereof. For example, the limb leads may comprise or consist: right arm (Red), left arm (Yellow), left leg (Green), right leg (Black), or any combination thereof. For example, the chest leads may comprise or consist: V1 (right sternal edge, 4th intercostal space), V2 (left sternal edge, 4th intercostal space), V3 (halfway between V2 and V4), V4 (position of the apex beat—e.g. intersection of the 5th intercostal space and mid-clavicular line), V5 (anterior axillary line), V6 (mid-axillary line), or any combination thereof. For example, the posterior leads may comprise or consist of V7 (left posterior axillary line, straight line from V6), V8 (left midscapular line, straight line from V7) and V9 (left paraspinal line, straight line from V8). For example, the anterior leads may comprise or consist: V1, V2, V3, V4, or any combination thereof. For example, the lateral leads may comprise or consist: V5, V6, I, aVL, or any combination thereof. For example, the inferior leads may comprise or consist: II, III, aVF, or any combination thereof.

The number of leads used in the method according to the present invention must exceed 2, and may be 5 or more, 10 or more, or 12 or more. Optionally, the number of leads do not exceed 4096. The plurality of leads of the present method may be 5, 12, 128 or 256 lead configurations.

The reference to "multiple time points" requires that the steps carried out at multiple time points are repeated a plurality of times. In other words, the methods of the present invention require more than one instance of the determining of a value derived from the output of a lead and which corresponds to an action potential (or diastolic interval). As it may be beneficial to evaluate changes in the relationship between action potential duration and diastolic interval achieved by the heart beating at different rates, each time point may be taken during a period in which the heart rate changes. The heart rate may be induced to change by: —the application of a chronotropic therapeutic agent to the subject in possession of the heart under analysis (ie medications that alter heart rate); by physically exercising the subject in possession of the heart under analysis; by providing electrical pacing impulses to the heart of varying frequency (often called "pacing spikes"). Alternatively, the electrical function of the heart may be analysed over a period (eg 48 hours) and the multiple time points chosen for analysis under the method of the present application as being those instances where extremes of heart rate are experienced (eg during a period of arrhythmia).

The action potential duration is the period of myocyte electrical activity, which would be understood to consist of the initial depolarisation, a plateau phase and finally repolarisation phase. The diastolic interval is the interval between action potentials, when the myocyte is electrically quiescent. The output from each lead of an ECG provides sufficient information concerning the electrical activity of the heart for a skilled person to derive therefrom a value for both the action potential duration and the diastolic interval. For example, the output of ECG leads may be converted into an ECG tracing, e.g. comprises a P wave, a QRS complex and a T wave. The skilled person would have no difficulty in preselecting the relevant portion of the ECG tracing that corresponds to the action potential duration and to the diastolic interval. By measurement of the duration of these preselected portions one can determine a value from the output of the lead and which corresponds to the action potential duration and to the diastolic interval.

The preselected portion that corresponds to the action potential duration can, for example, be the QT or the JT interval. The preselected portion that corresponds to the diastolic interval can, for example, be the TQ interval. The process of determining the value for each lead in step a. should be consistent. The process of determining the value for each lead in step b. should be consistent.

It should be understood that how one precisely calculates the beginning and end of each of these intervals (in order to identify their duration) is of less significance than the fact that the value for the JT, QT and TQ intervals is measured for each in the methods of the present invention in a consistent manner. For example, the QT interval may be measured: —from the beginning of the QRS complex to the end of the T wave; from the onset of the R wave to the end of the T wave; from the beginning of the QRS complex to the peak of the T wave, or; from the onset of the R wave to the peak of the T wave. For example, the JT interval may be measured: —from the point of separation between the QRS complex and the end of the T wave, or; from the point of separation between the QRS complex and the peak of the T wave. For example, the TQ interval may be measured: —from the end of the T wave to the beginning of the QRS complex; from the end of the T wave to the onset of the R wave; from the peak of the T wave to the beginning of the QRS complex, or; from the peak of the T wave to the onset of the R wave. (see, for example, Malik et al.; JACC; 2000; 36:1749-66). When the heart rate is under the influence of electrical pacing impulses, during capture of values for the present method, the pacing spikes that appear in an ECG and that correspond to each pacing impulse may be taken to be the beginning of the action potential duration and/or the end of the diastolic interval.

Determining a relationship between the determined values for action potential duration and diastolic interval across the multiple time points may be achieved in a number of ways, which would be understood by the skilled person. For example, a restitution curve for each lead may be plotted on a graph (conventionally, the Y-axis corresponds to the action potential duration, whilst the x-axis corresponds to the diastolic interval). A restitution curve for a individual heart cell describes the nonlinear relationship between the Diastolic Interval and Action Potential Duration. Establishing a restitution curve is well within the ordinary skill in the art. For example, an explanation as to how to establish a restitution curve suitable for use in the present invention may be found in Taggart et al. "Effect of Adrenergic Stimulation on Action Potential Duration Restitution in Humans" Circulation, 30 Dec. 2002 (incorporated herein by reference), ie a method that uses least squares regression to fit a linear gradient within a 40 ms segment of the data. This segment is then moved in 10 ms increments along the x-axis (TpQ).

The characteristic of interest is optionally any characteristic that defines the change in the aforementioned relationship between action potential duration and diastolic interval as seen by each lead. Consequently, the characteristic of interest may be one or more gradient of the restitution curve for each lead, optionally the gradient of the restitution curve at each time point on that curve and for each lead. Each point plotted to establish a restitution curve for each lead represents the relationship between action potential duration and diastolic interval at the time-point when the output was received from that lead. The gradient of the curve passing that point may be calculated as the characteristic of interest. Rather than analysing each time point on that curve for each lead, time points on only a portion of the curve for each lead may instead be analysed. For example, analysing only the first quarter of time points, the second quarter of time points, the third quarter of time points and/or the fourth quarter of time points. Rather than analysing each time point on that curve, or portion of that curve, a representative selection of time points instead may be only analysed. For example, only every 2nd, 3rd, 4th, 5th, or 6th time point in the curve or portion of the curve may be analysed. Indeed, the method does not have to be restricted to time-points on the curve for each lead being time points that are directly derived from the diastolic interval and action potential duration values derived from the output of the leads. Once the curve has been established, every point along the curve may be taken as a time point (including those in the curve that are positioned between points directly derived from the action potential duration and diastolic interval values derived from the output of leads). The combined value may be a plurality of combined values, each combined value being a combining of information for the characteristic for each time point. The combined value may be an average of the characteristic of interest across the leads for each time point, and so a combined value for one or more time point may be derived. This is quite distinct from establishing the amount of difference between the characteristics for each time-point. For example, when the characteristic of interest is a gradient of the restitution curve at a time point, the combined value, or one of the combined values, is obtained by establishing the average value for the gradient across the leads, optionally the combined value is obtained by establishing, for each time point, the average value for the gradient across the leads for one time point. This would, for example, require establishing the gradient for the time-point established by each lead, the average of those gradients is then established. Establishing an average is well within the skill of the ordinary person. Any method may be used as long as it is consistently used. For example, all values may be added together and the total is divided by the number of values in order to identify the average value.

The analysis of step d) may comprise the identification of the steepest gradient from the combined values. For example, if multiple time points are analysed and so multiple combined values are determined, the value of the steepest of the gradients (ie the highest combined value) may be the combined value used in step e.

It has been found that the steeper the gradient the more likely the subject is going to progress to cardiac failure, and so be more likely to require a implantable cardioverter defibrillator or the need for administration of anti-arrhythmic agents. For example a gradient of greater than 1.21 is considered to be indicative of an elevated risk of developing a cardiac arrhythmia or cardiac failure compared to normal (as analysed by the methods of the present invention), for example analysed according to the Peak Electrocardiogram Restitution Gradient (PERG) as described later in the methods section.

It has been found that analysis using the aforementioned method when combined with the R2I2 method results in a more accurate assessment of cardiac function. R2I2 identifies the amount of difference between the relationships identified in step c, and the greater the amount of difference between each lead, the greater the risk of developing cardiac arrhythmia. Consequently, the methods of the present invention may include the additional steps of carrying out analysis according to R2I2 (as described in WO 2011/117608 A1 or Nicolson et al. "A Novel Surface Electrocardiogram-Based Marker of Ventricular Arrhythmia Risk in Patients with Ischemic Cariomyopathy" J. American Heart Association, 2012 and incorporated herein by reference) and combining that analysis with that carried out in step e. of the present invention.

For example, the method of the present invention may additionally comprising the steps of: —
f. assessing the differences between the determined relationships from step c) for each of the plurality of leads.
g. assessing the cardiac function of the heart, determining the subject's need for the implantation of an implantable cardioverter defibrillator, or the need for administration of an anti-arrhythmic agent by analysing the combined assessment of step e. and step f.

There are many ways in which the difference between the relationships identified in step c. may be assessed in step f. For example, the relationship between single action potential duration and a single diastolic interval may be determined as a ratio of the two for each lead, the difference between the ratios for each lead may be assessed numerically. For example, when a number of action potential durations and diastolic intervals are determined for each lead, the differences between the determined relationships may be assessed by identifying or quantifying the difference in the gradient or gradients of the curves established by plotting the values for action potential duration against diastolic interval (or vice versa) for each lead on a graph (ie a restitution curve). This difference may be visually apparent from degree of separation of the curves for each lead over the length of the curves, or by changes in the degree of separation of the curves for each lead over the length of the curves.

Numerical analysis of the curves may also be used to quantify the differences. For example, the following process may be applied: —(1) application of logistic regression to the data set to derive a polynomial equation, (2) application of this polynomial equation, adjusting the linear constant to achieve best fit, to each lead in turn, (3) using logistic regression to calculate the residuals this technique produces for each lead, (4) Summing the residuals will produce a measure of the differences between the relationships. At point (1) a spline could be used in place of the polynomial equation. At point (1) linear regression could be used separately on groups of leads from each cardiac region, the resulting equations could then be applied to the leads from their corresponding regions as described in steps (2), (3) and (4). In a further example, the following process may be applied: —(1) the standard deviation of the action potential difference from all leads is calculated for each determined diastolic interval length, (2) the mean of this value is taken as a marker of heterogeneity of the data For example, assessing the difference in step f may comprise, for each time point: —
(i) establishing the mean point between the relationships determined in step c. for each of the plurality of leads,
(ii) for each lead, calculating the square of the residual from the mean point to the relationship determined for that lead (e.g. the square of the variation from the mean);

Assessing the difference in step f may further comprise: —
(iii) for each lead, calculating the mean value of the square of the residuals calculated in step (ii) for each time point.

Assessing the difference in step f may further comprise: —
(iv) calculating the normalised mean value by dividing the mean value calculated in step (iii) by the same mean value when calculated from the assessment of subjects at normal risk of developing cardiac arrhythmia, or by the mean of the values of step (iii) for all of the plurality of leads.

Assessing the difference in step f, may further comprise: —
(v) identifying the largest normalised mean value calculated in step (iv) out of the normalised mean values calculated for each of the plurality of leads.

The values calculated in step (v) have been designated the Regional Repolarisation Instability Index (R2I2).

It has been found that the greater the difference between the relationships identified for each lead (which can be demonstrated by a relatively large R2I2), the greater the risk that the heart being assessed is abnormal, eg will develop a cardiac arrhythmia. Thus, the method of the present invention, when applied to the outputs derived from an ECG applied to a subject, may be used as in a method of prognosis to assess the risk of the subject developing arrhymia. Essentially, therefore, an increased level of heterogeneity between the relationships determined for each lead (which can be demonstrated by a relatively large 8212) results in an increased risk of cardiac arrhythmia.

Consequently, in one embodiment of the present invention, the steps of the invention may be carried out on the output derived from an ECG applied to a subject to be examined for the risk of developing cardiac arrhythmia. The method may further comprise the carrying out of the steps on the output derived from an ECG applied to a subject that has been determined to have normal risk of developing cardiac arrhythmia, and comparing the differences in step f assessed for the output from the subject to be examined with the differences in step f. assessed for the output from the subject determined to be at normal risk of developing cardiac arrhythmia (or a predetermined value that corresponds to the differences in step d. assessed for the output from subjects determined to be at normal risk of developing cardiac arrhythmia). When the differences are determined to be greater for the subject to be examined than those of the subject determined to be at normal risk (or than the predetermined value), the subject to be examined is at increased risk of developing a cardiac arrhythmia (increased, being at greater risk than normal or vice versa). Similar analyses with respect to a normal subject may be carried out with respect to step e.

The predetermined value is derived from the assessment of subjects determined to be at normal risk of developing cardiac arrhythmia (i.e. the mean value for a group of normal subjects). Normal subjects therefore represent a control group. Determining whether or not an individual subject is normal with respect to their risk of cardiac arrhythmia is a clinical question well within the abilities of the skilled person. However, in the interests of clarity, but not wishing to be restricted further, individuals in such a group will be characterised by structurally normal heart, as determined by echocardiography, and no history of palpitation, syncope or other cardiac problems. Optionally a normal subject has no family history of cardiac death.

If both steps e and g conclude that there is an increased risk of the heart having less than normal function (ie the subject for the heart is at increased risk of developing a cardiac arrhythmia than normal) the risk is determined to be greater than if only steps e or g had that conclusion.

In a second aspect of the present invention there is provided a method for determining a subject's need for the implantation of an implantable cardioverter defibrillator or the need for administration of an anti-arrhythmic agent, comprising the steps of: —
 a. for each of a plurality of leads of an ECG directed to the subject, at multiple time points, determining a value derived from the output of that lead and which corresponds to an action potential duration;
 b. for each of the plurality of leads of the ECG directed to the subject, at the multiple time points, determining a value derived from the output of that lead and which corresponds to a diastolic interval;
 c. for each of the plurality of leads of the ECG directed to the subject, using the determined values for action potential duration and diastolic interval across the multiple time points to determine a relationship between action potential duration and diastolic interval as seen by that lead;
 d. defining at least one characteristic of interest of each of the determined relationships between action potential duration and diastolic interval and combining information on that characteristic from the relationships seen by the plurality of leads to derive a combined value;
 e. deriving an assessment of the subject's need for the implantation of an implantable cardioverter defibrillator or the administration of an anti-arrhythmic agent based on the analysis of the combined value.

Such a method can be used in a method for directing subjects determined to need treatment to be treated with by administering of an effective amount of one or more anti-arrhythmic agent, and/or to be treated by implanting a cardioverter defibrillator.

Such a method can be used in a method of treating a subject with cardiac arrhythmia and further comprises the step of administering an effective amount of one or more anti-arrhythmic agent to a subject, and/or implanting a cardioverter defibrillator if the subject is assessed by step d. to require such treatment.

Any clinically relevant anti-arrhythmic agent may be used, for example amiodarone.

In order to monitor the efficacy of any anti-arrhythmic agent, the methods of the present invention may be carried out first in the absence of treatment with an anti-arrhythmic agent and then repeated one or more times after the administration of one or more doses of anti-arrhythmic agent. In this way the methods of the present invention may be used to track the efficacy of treatment using the agent.

All optional features of the first aspect of the present invention maybe included in the second aspect of the present invention. For the avoidance of doubt, it should be understood that when the method identifies that the subject is at increased risk of developing cardiac arrhythmia, there is an increased need for the implantation of an implantable cardioverter defibrillator in the subject or the administration of an anti-arrhythmic agent to the subject (e.g. compared to an individual at normal risk of developing cardiac arrhythmia).

In a third aspect of the present invention there is provided Apparatus for assessing the function of the heart, comprising a computer arranged to receive input from each of a plurality of leads of an ECG and arranged to: —
 a. for each of a plurality of leads of an ECG, at multiple time points, determining a value derived from the output of that lead and which corresponds to an action potential duration;
 b. for each of the plurality of leads of the ECG, at the multiple time points, determining a value derived from the output of that lead and which corresponds to a diastolic interval;
 c. for each of the plurality of leads of the ECG, using the determined values for action potential duration and diastolic interval across the multiple time points to determine a relationship between action potential duration and diastolic interval as seen by that lead;
 d. defining at least one characteristic of interest of each of the determined relationships between action potential duration and diastolic interval and combining information on that characteristic from the relationships seen by the plurality of leads to derive a combined value;
 e. deriving an assessment result by analysing the combined value.

The apparatus according to the third aspect of the present invention is arranged so as to be capable of operating the methods according to the earlier aspects of the present invention. Consequently, all features of the first and second aspects of the present invention maybe included in the third aspect of the present invention. For example: —

The apparatus may include an ECG device. The ECG device may include a plurality of electrodes configured to provide any of the lead combinations described for the first aspect of the present invention.

The output from each lead of an ECG provides sufficient information concerning the electrical activity of the heart for the computer to derive therefrom a value for both the action potential duration and the diastolic interval. For example, the computer may be configured to convert the output of ECG leads into an ECG tracing, e.g. comprises a P wave, a QRS complex and a T wave. The computer may be configured to preselect the relevant portion of the ECG tracing that corresponds to the action potential duration and to the diastolic interval. Appropriate pre-selection criteria are discussed above with respect to the first aspect of the present invention.

The computer may be arranged to determine the relationship between the action potential duration and the diastolic interval in a number of ways, see for example the determination discussed in the first aspect of the present invention The apparatus of the present invention, when applied to the outputs derived from an ECG applied to a subject, may be used in a method of prognoses of the risk of that subject developing cardiac arrhythmia.

The apparatus may further comprise an electrophysiological catheter capable of providing an electrical provocation to the cardiac tissue.

The apparatus may further comprise a computer program product that when run on the computer causes it to be configured in the aforementioned manners.

In a fourth aspect of the present invention, there is provided a computer program product when run on a computer arranged to receive input from each of a plurality of leads of an ECG causes the computer to: —
  a. for each of a plurality of leads of an ECG, at multiple time points, determining a value derived from the output of that lead and which corresponds to an action potential duration;
  b. for each of the plurality of leads of the ECG, at the multiple time points, determining a value derived from the output of that lead and which corresponds to a diastolic interval;
  c. for each of the plurality of leads of the ECG, using the determined values for action potential duration and diastolic interval across the multiple time points to determine a relationship between action potential duration and diastolic interval as seen by that lead;
  d. defining at least one characteristic of interest of each of the determined relationships between action potential duration and diastolic interval and combining information on that characteristic from the relationships seen by the plurality of leads to derive a combined value;
  e. deriving an assessment result by analysing the combined value.

The computer program according to the fourth aspect of the present invention may be included in the apparatus of the third aspect of the present invention. Consequently, all features of the previous aspects of the present invention maybe included in the fourth aspect of the present invention.

In yet a further aspect of the present invention, there is provided a method as substantially hereinbefore described and with reference to the figures.

In yet a further aspect of the present invention, there is provided apparatus as substantially hereinbefore described and with reference to the figures.

In yet a further aspect of the present invention, there is provided a computer program as substantially hereinbefore described and with reference to the figures.

The present invention will now be described, by way of example, with reference to accompanying figures, in which.

Figure 5:
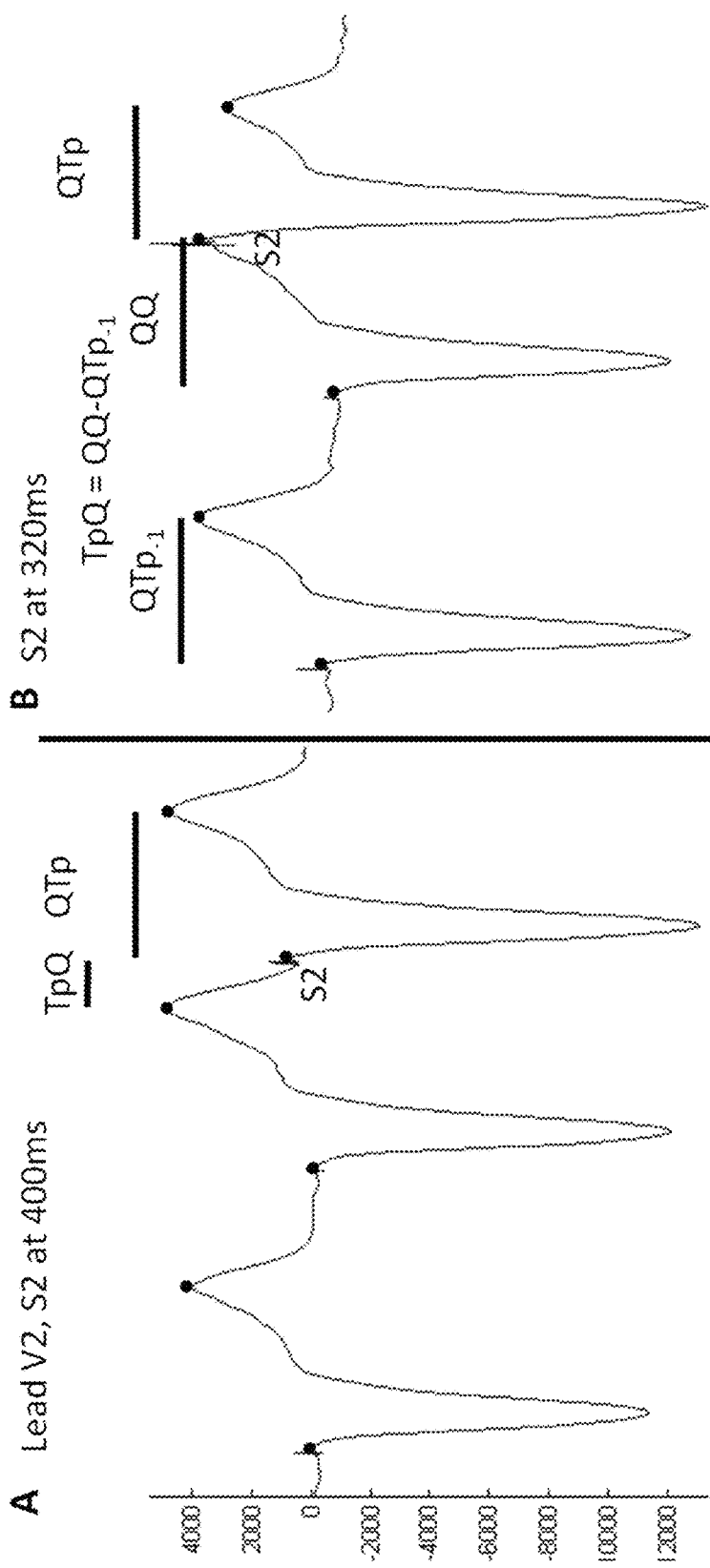

FIG. 5 shows the technique by which TpQ and QTp measurements are made: when an S2 arrives after the T wave peak the TpQ and QTp are measured as shown on the left of the diagram. However, if the S2 occurs before the T wave peak the TpQ is effectively negative. In this case it is measured by subtracting the QTp1 interval (QTp for drive cycle beat) from the QTp2, in the example above this would give a TpQ close to zero.

Figure 6:
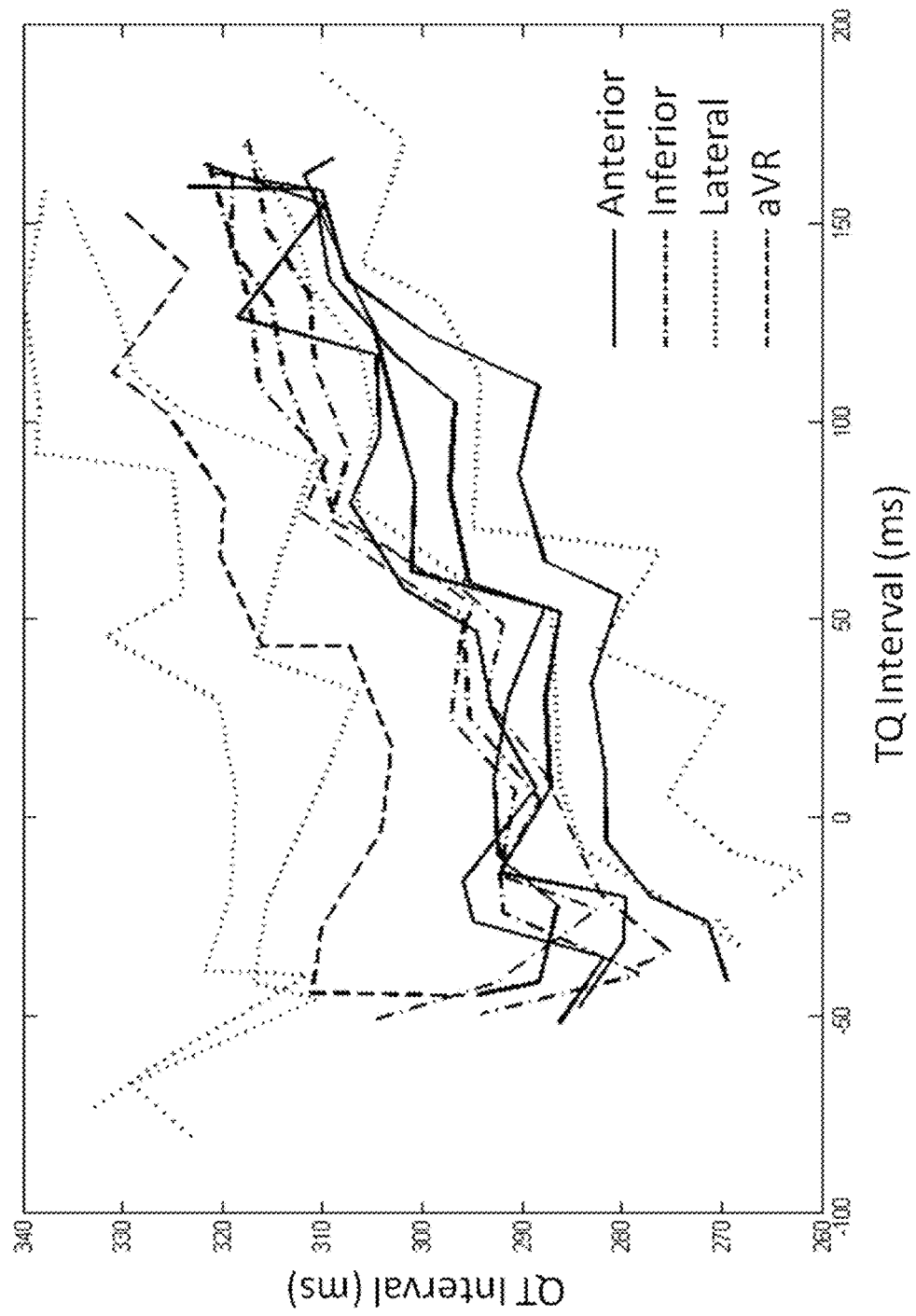

FIG. 6 is a graph that illustrates the dynamic relationship between QTp interval and TpQ interval for 12 leads, marked to show the 4 lateral leads, 3 inferior leads, 4 anterior leads and 1 aVR lead. Results for population mean values of all patients in the study shown on the graph.

Figure 7:
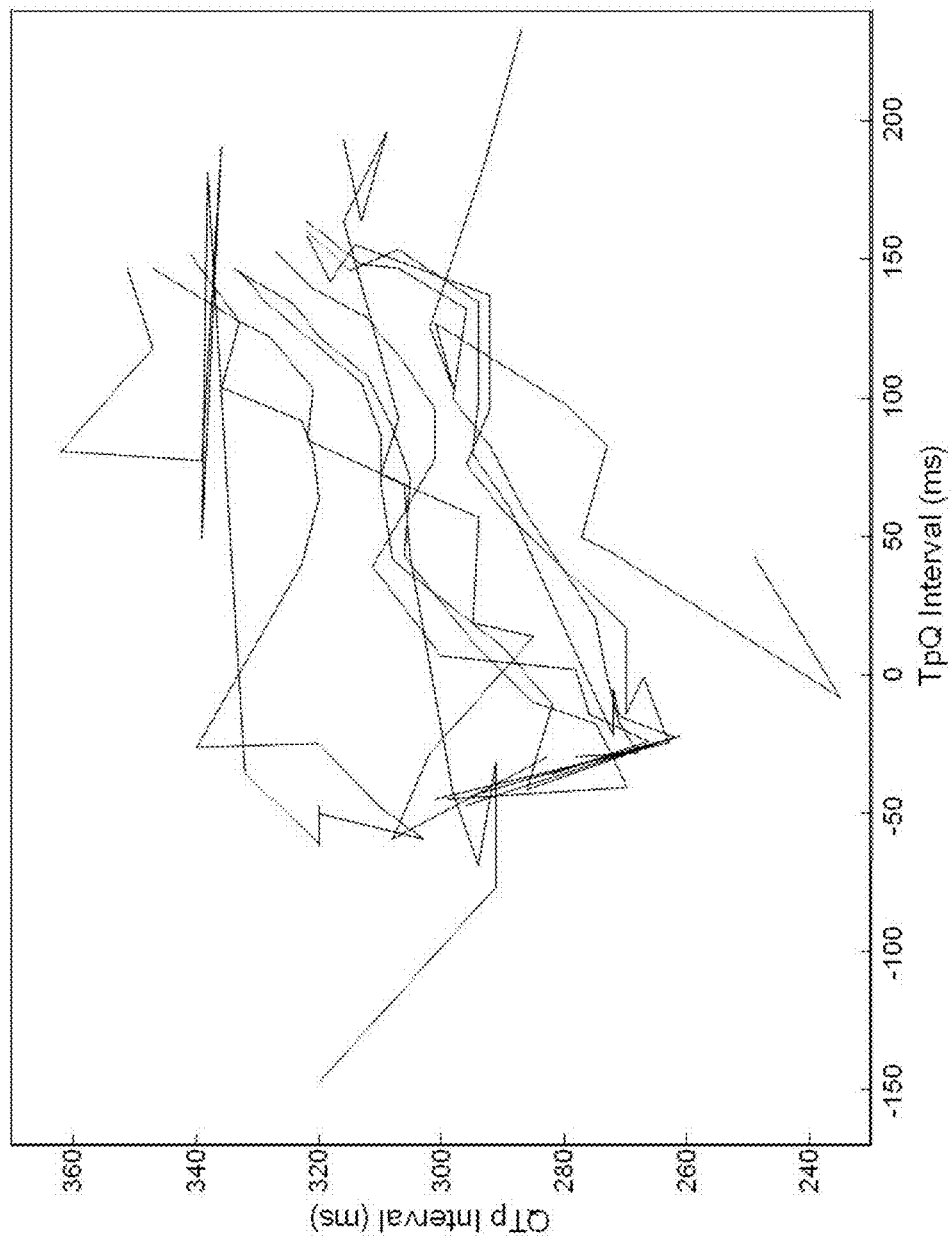

FIG. 7 is a graph that illustrates the dynamic relationship between QTp interval and TpQ interval for 12 leads prepared for the assessment of R2I2 of a single patient.

Figure 8:
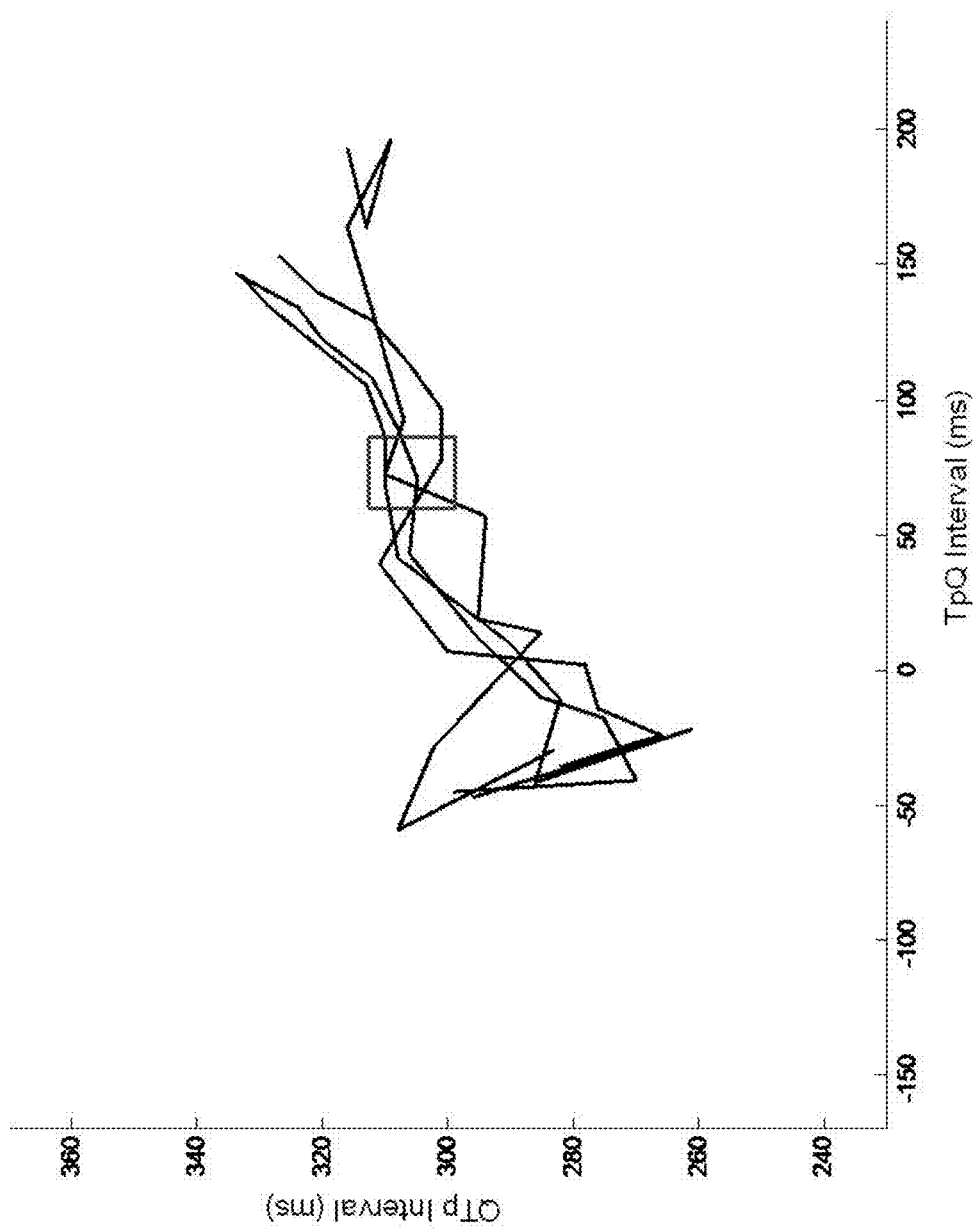

FIG. 8 provides a selection of only the anterior leads of the graph of FIG. 7, prepared for the assessment of R2I2.

Figure 9:
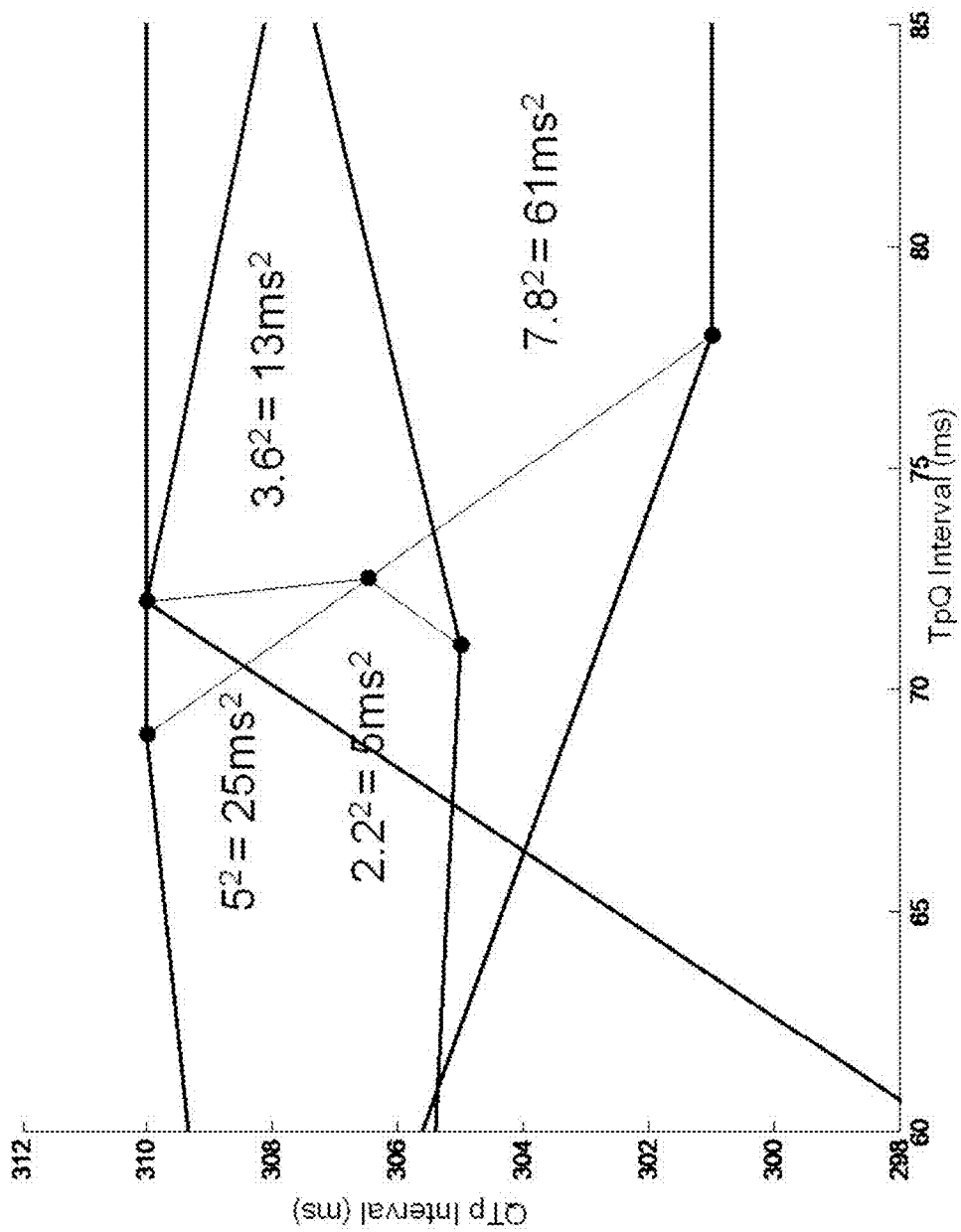
Figure 10:
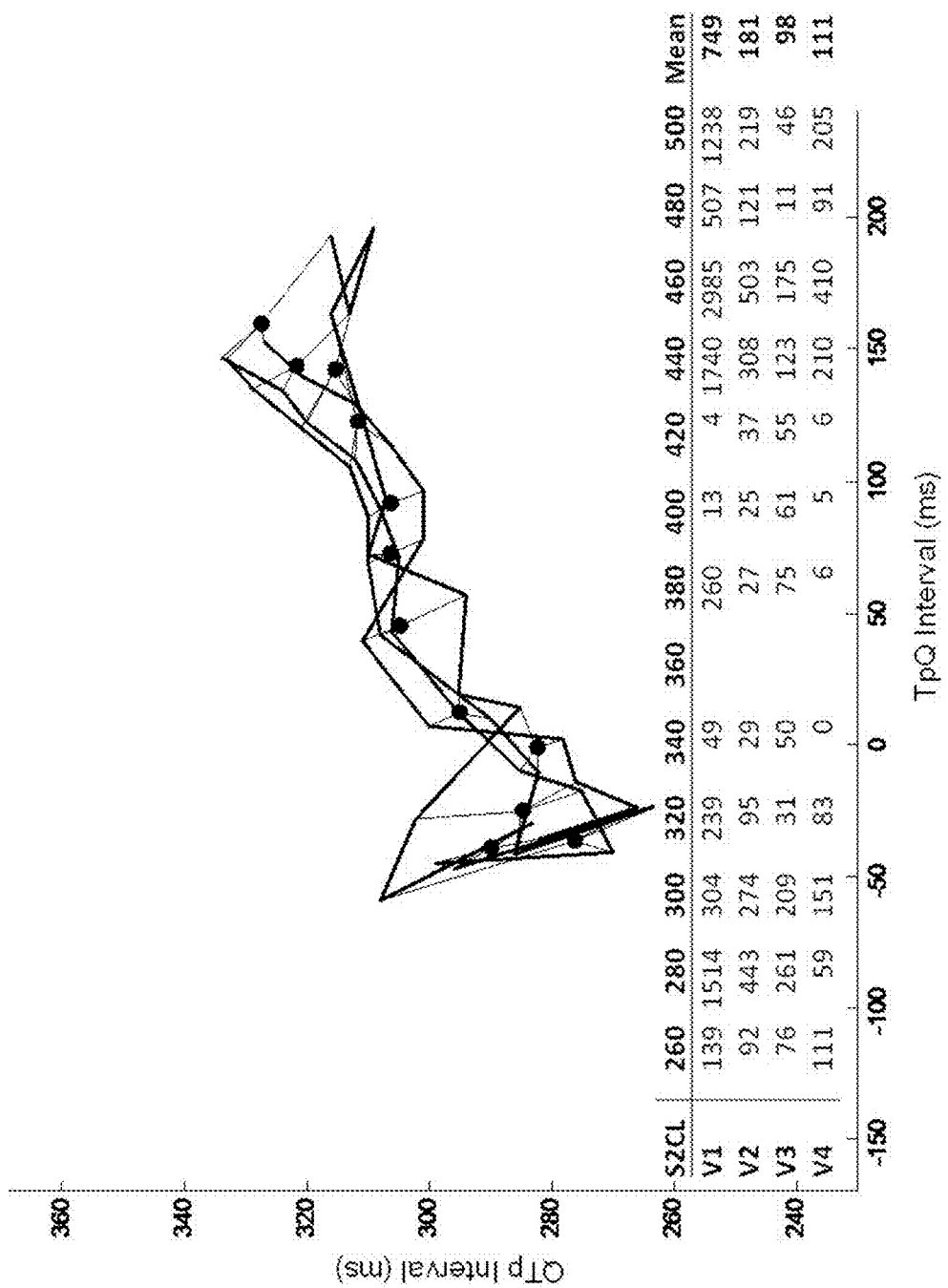

FIG. 9 provides a blown up image of the box provided in the graph of FIG. 8. This figure also illustrates how to establish the mean point between the relationships determined for this repetition for each of the anterior leads, and then how to calculate the square of the residual from the mean point to the relationship determined for each lead (e.g. the square of the variation from the mean);

FIG. 10 represents the graph of FIG. 8 with the mean points for each repetition provided in the graph, with figures provided below.

Figure 11:
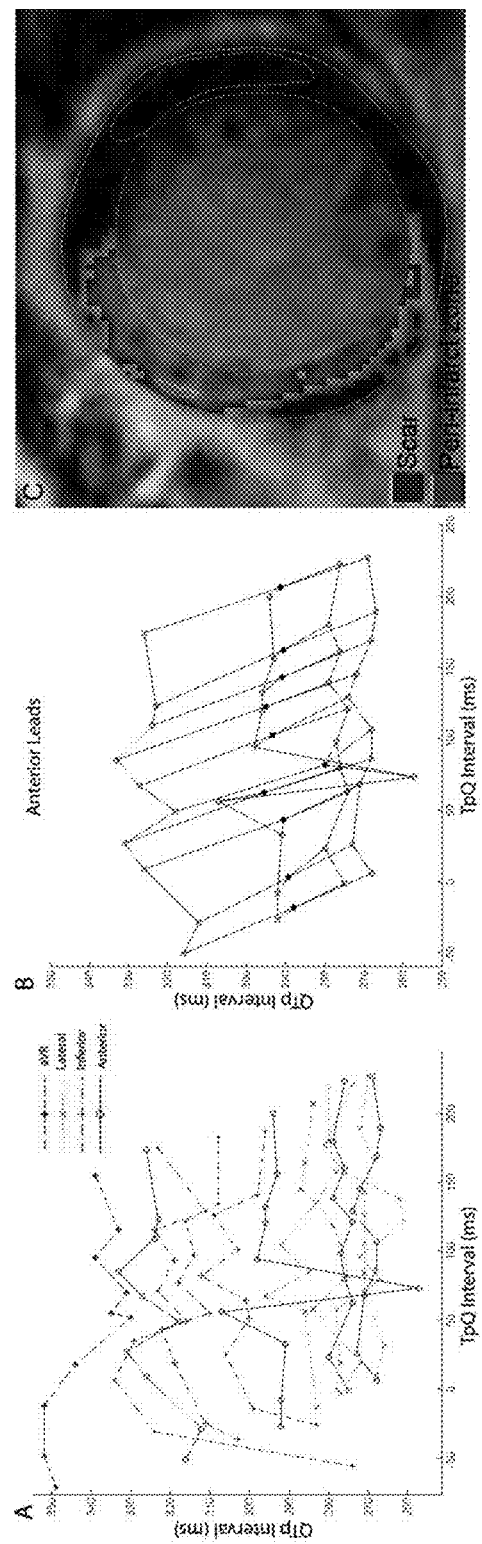

FIG. 11 provides an explanation of the R2I2 calculation: the graph in A shows the anterior, inferior and lateral leads for a patient who reached the endpoint of ventricular arrhythmia (VA)/death. Each region is analysed separately as seen for the anterior leads in B; the points are grouped by the S1 S2 coupling interval that produced them and the square of the residuals (narrow black lines) from best fit points (black dots) is calculated for each lead at each S1 S2 coupling interval. The mean of these residuals is then taken for each lead. There were differences in the spread of the leads, in particular the lateral leads tended to be more widely spaced than the anterior and inferior leads. A proportion was therefore taken: each lead's value was divided by the population mean value for that lead. The R2I2 is then taken as the mean of the maximum anterior, inferior and lateral values. The LGE CMR scan for this patient (C) showed a large anteroseptal and apical myocardial infarction with 16% peri-infarct zone (PIZ) anteriorly, 13% inferiorly and 4% laterally corresponding with the R2I2 components: anterior 3.6, inferior 1.3 and lateral 0.25.

Figure 12:
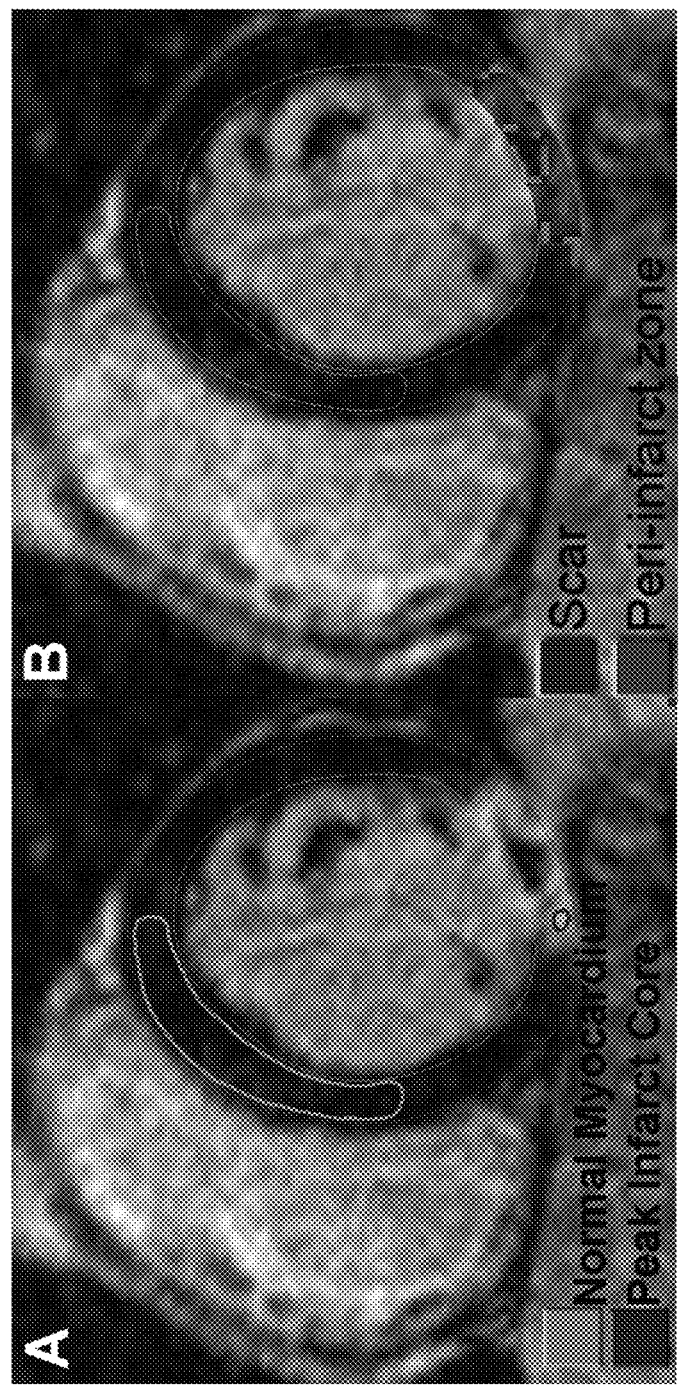

FIG. 12 shows a cardiac magnetic resonance scan. A) First endocardial and epicardial borders are drawn; then a large representative area of "normal myocardium" and a small area of "peak scar" are selected. B) Software analysis identifies all voxels with signal intensity >2 standard deviations (SD) above "normal myocardium" mean intensity and voxels with signal intensity >50% of the "peak scar" are subtracted from this to obtain the PIZ. Identified voxels that are not in the region of an infarct are discarded. The example in B shows an infarct with relatively small PIZ compared with the example in FIG. 11C.

Figure 13:
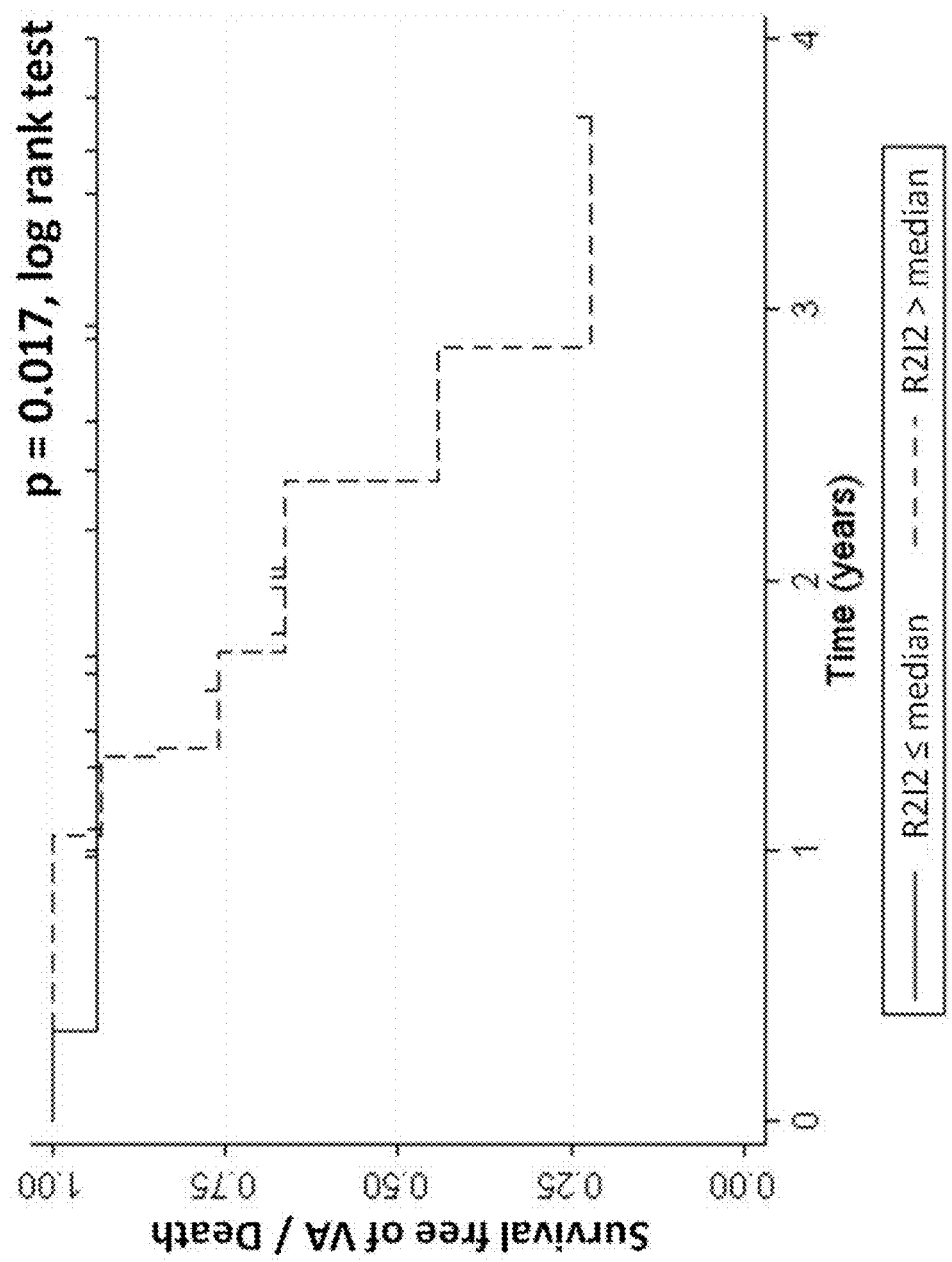

FIG. 13 shows a Kaplan-Meier curve of the probability of survival free of ventricular arrhythmia (VA)/death in the "high risk" group with R2I2>median and the "low risk" group with R2I2<=median. The difference in VA/death was significant (p=0.017, log rank test).

Figure 14:
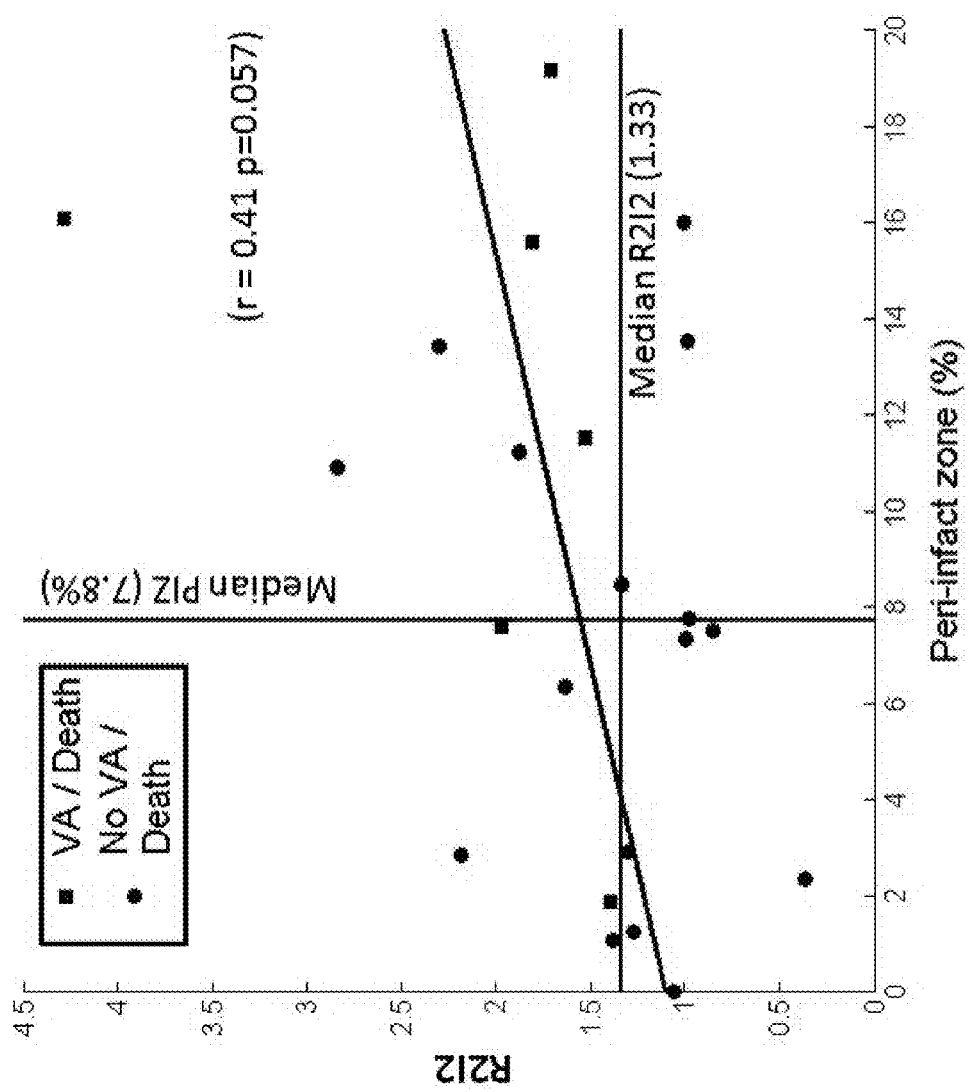

FIG. 14 shows a plot of R2I2 against PIZ in each of the 22 patients for whom paired data was available. Lines are drawn at the median values for both parameters. A least-squares regression line demonstrates a degree of correlation (r=0.41 p=0.057).

Figure 15:
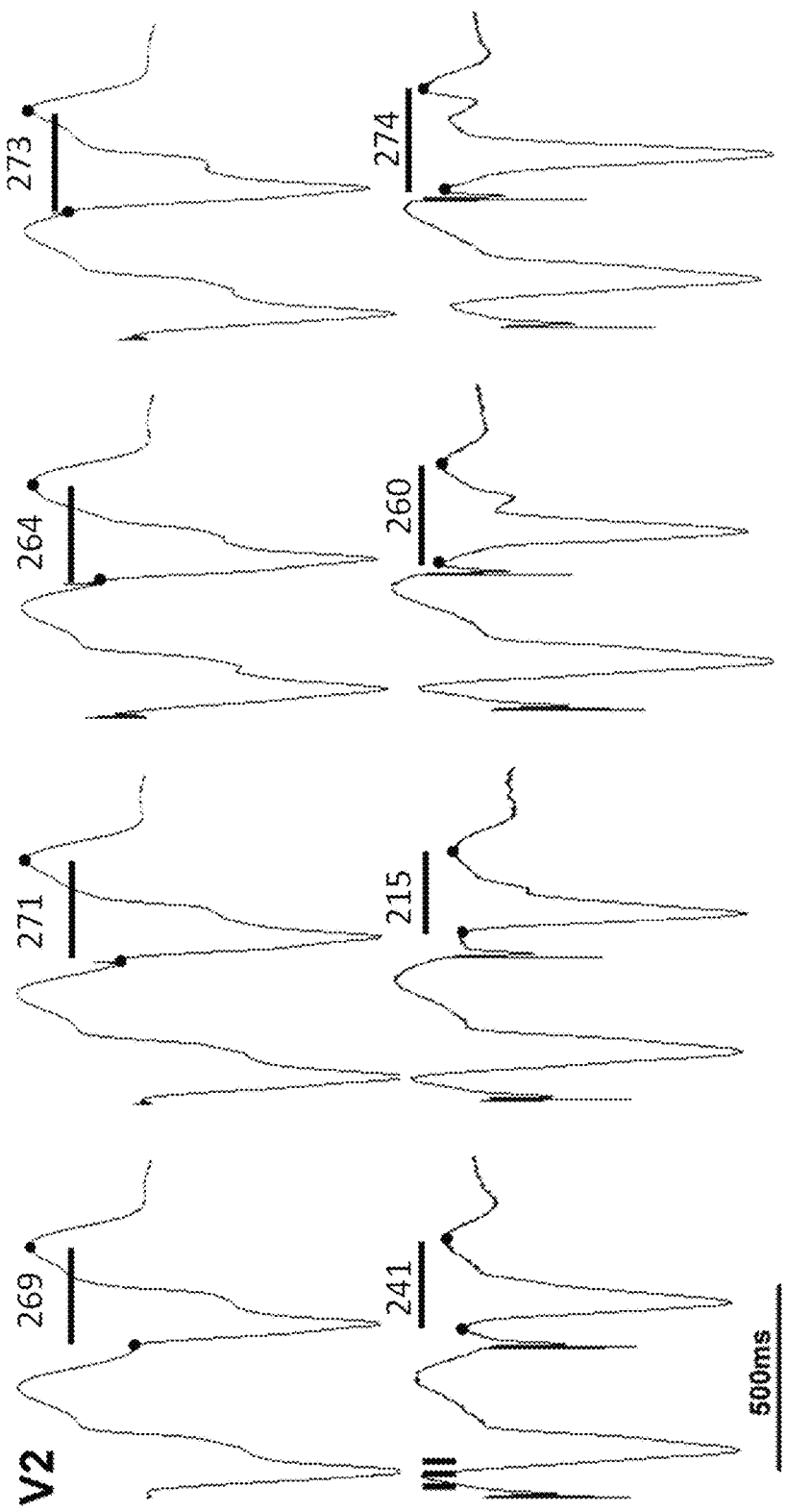

FIG. 15 shows a diagram of the last beat of the drive train and the S1 S2 coupling interval at 400, 380, 360 and 340 ms for leads V2 and III. Demonstration of regional heterogeneity in repolarisation: little change is seen in V2 and the QTp is stable, while lead III is seen to fragment with two peaks and variable QTp. This gross change was seen in 2/4 of the patients who developed VA during follow up.

Figure 16:
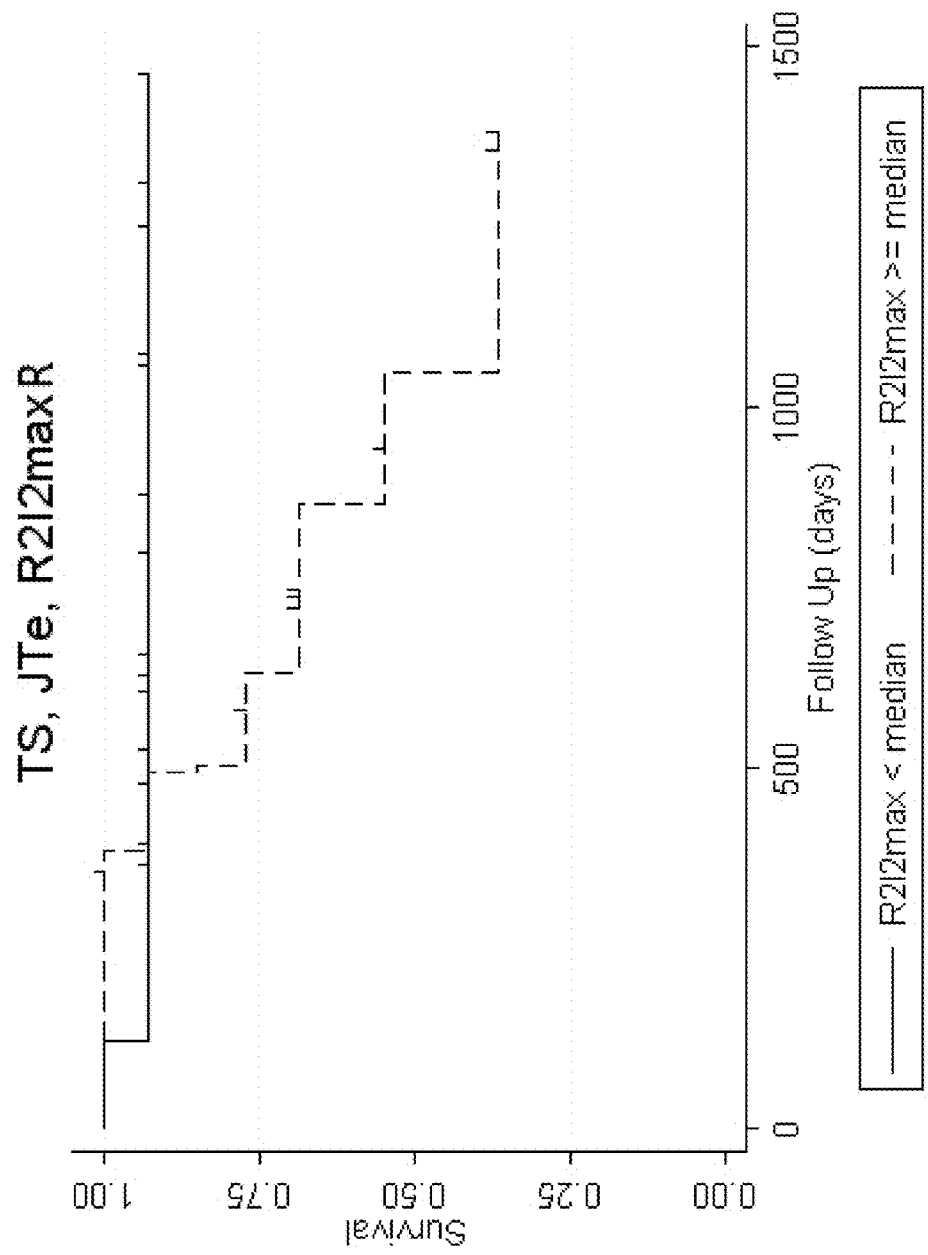

FIG. 16 shows a Kaplan-Meier curve of probability of survival free of VA/death in "high risk" group R2I2maxR>median and the "low risk" group with R2I2maxR<=median. The difference in VA/death was significant (P=0.051 log rank test). Here the R2I2maxR has been calculated using TpS in place of the TpQ and JTe in place of the QTp. Additionally the maximum normalised mean value has been taken rather than the mean of the regional normalised mean maxima.

Figure 17:
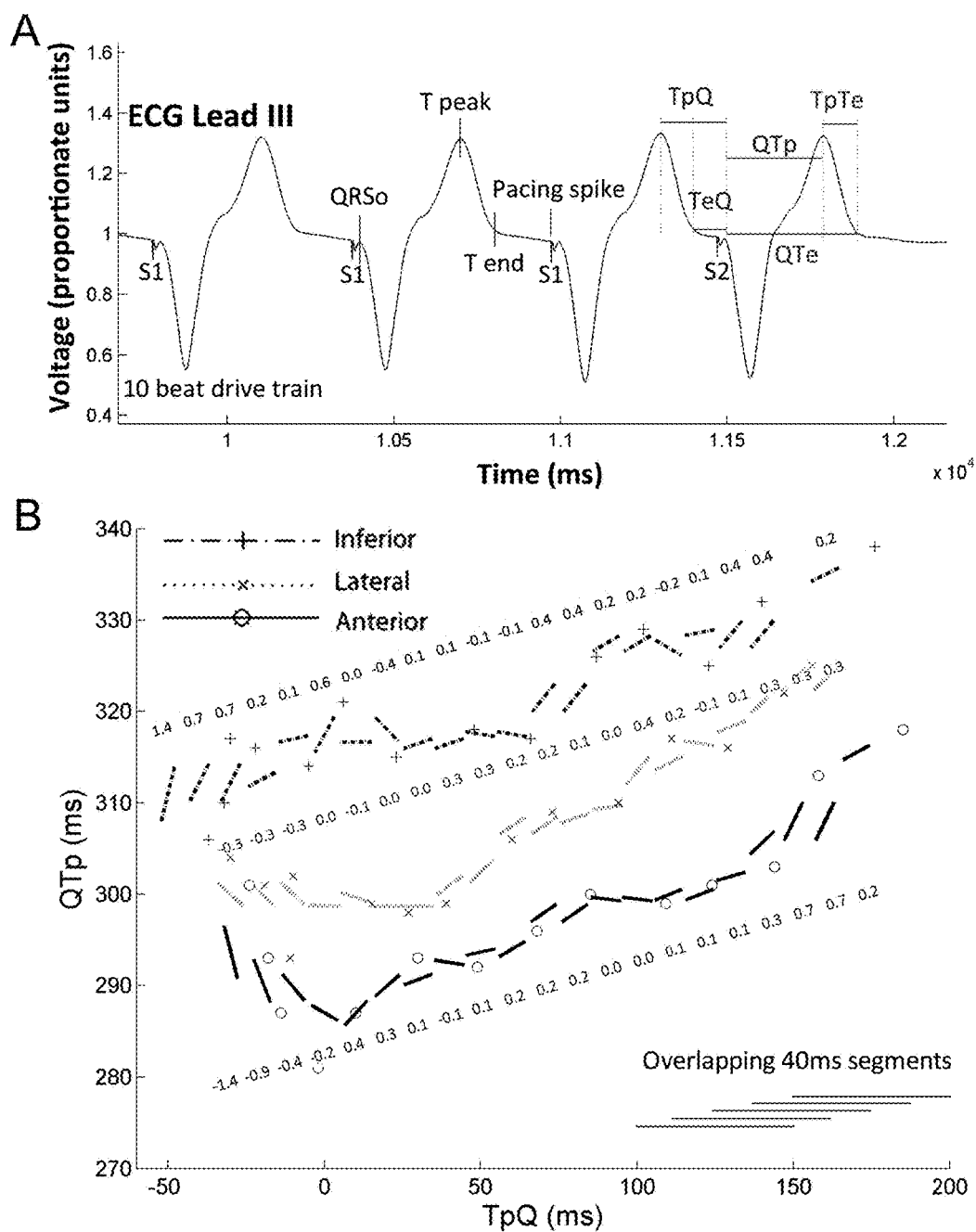

FIG. 17 shows measurement of R2I2. FIG. 17A: Lead III example of Identification of ECG fiducial points. Last 3 beats of drive train (S1) and extrastimulus (S2) beats shown. Paired surrogates for APD/DI shown; both QTe and TpTe are paired with TeQ. Abbreviations: TpQ T wave peak to QRS onset, TeQ T wave end to QRS onset, QTp QRS onset to T wave peak, QTe QRS onset to T wave end, TpTe T wave peak to T wave end. FIG. 17B: QTp/TpQ plot for representative ECG leads: V2 (anterior), II (inferior) and aVL (lateral) to explain the Regional Restitution Instability Index (R2I2) calculation in a typical study patient. For each lead, the QTp/TpQ gradient (least squares regression) was calculated over a 40 ms segment of TpQ range. This segment was then scanned over the range of TpQ with available data to produce gradients at 10 ms intervals (numerical gradients are shown in bars adjacent to the corresponding lines, note on the far left gradients are available for lead II but not for V2 and aVL). The difference of the gradient from the mean gradient in each 40 ms segment was calculated. The standard deviation of these values was taken as a measure of action potential duration restitution heterogeneity within each lead. The mean of this was then taken as the R2I2.

Figure 18:
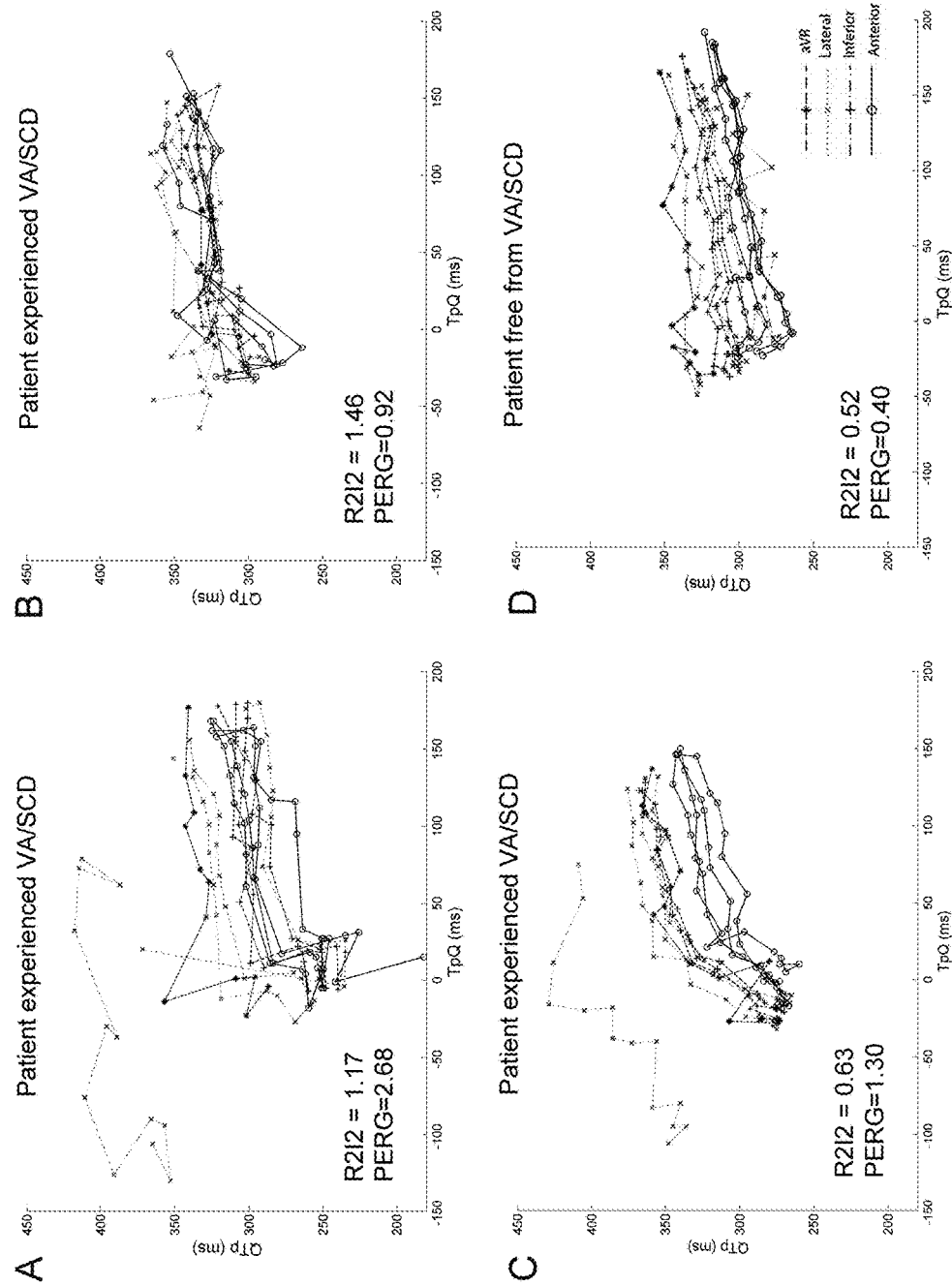

FIG. 18 shows QTp/TpQ plots for 4 patients with A. high R2I2 and high PERG, B. high R2I2 and low PERG, C. low R2I2 and high PERG, D. low R2I2 and Low PERG. For each example patient the 12 ECG leads have separate lines styles coded by ECG region. The lines are drawn point-to-point rather than as gradients to allow differentiation of the ECG leads. R2I2 is higher in the patients whose ECG leads follow dissonant QTp/TpQ paths. PERG reflects the steepest gradient taken as a mean for all 12 ECG leads.

Figure 19:
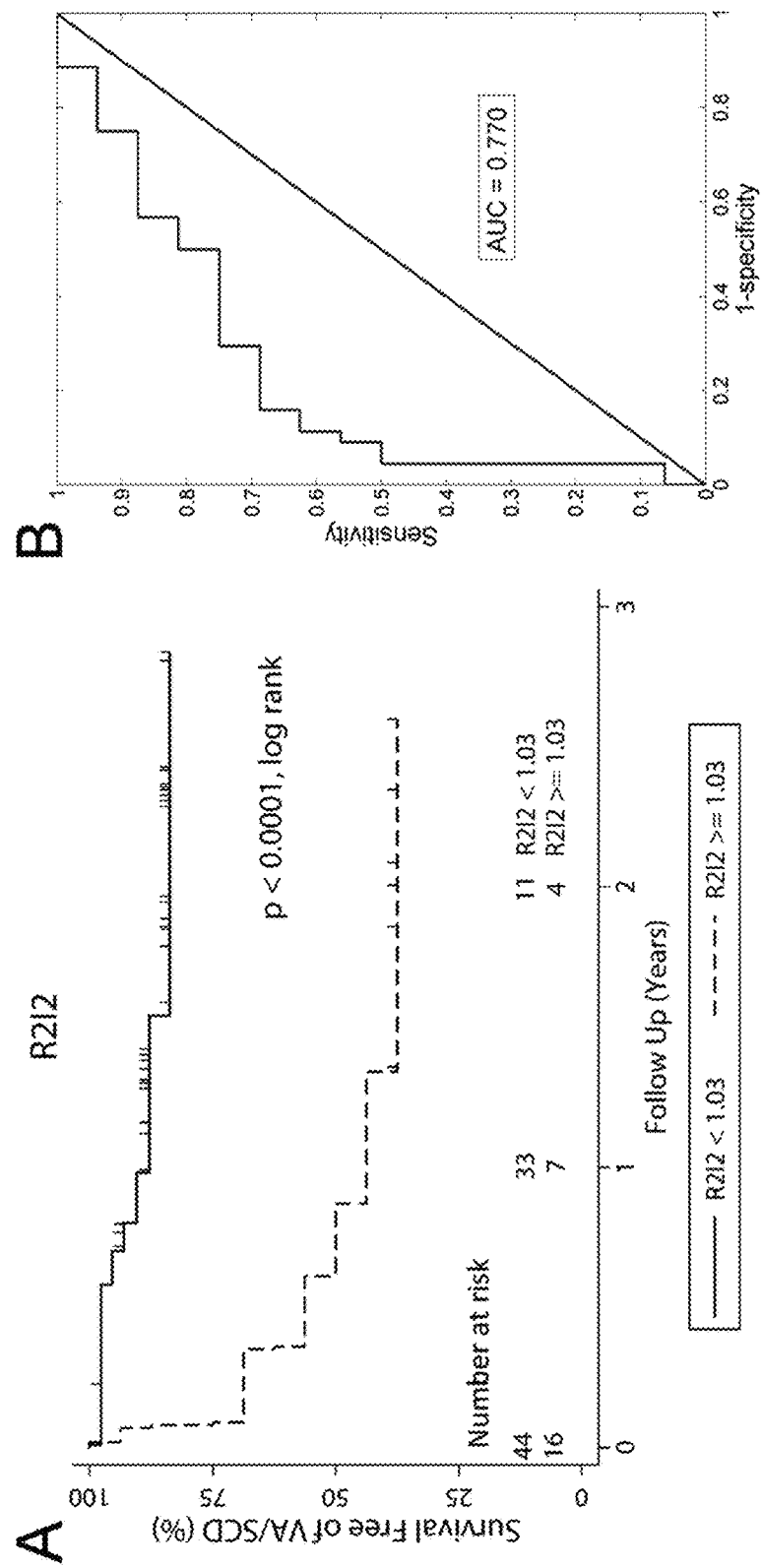

FIG. 19 shows association of R2I2 with risk of ventricular arrhythmia/sudden cardiac death. FIG. 19A: Kaplan Meier curve showing significant separation of the curves for survival free of ventricular arrhythmia/sudden cardiac death for patients partitioned by an R2I2 value of 1.03 (p<0.0001, log rank). FIG. 19B. Receiver operating characteristic curve for Regional Restitution Instability Index (R2I2): VA/SCD vs. event free survival. (Area under curve=0.770)

Figure 20:
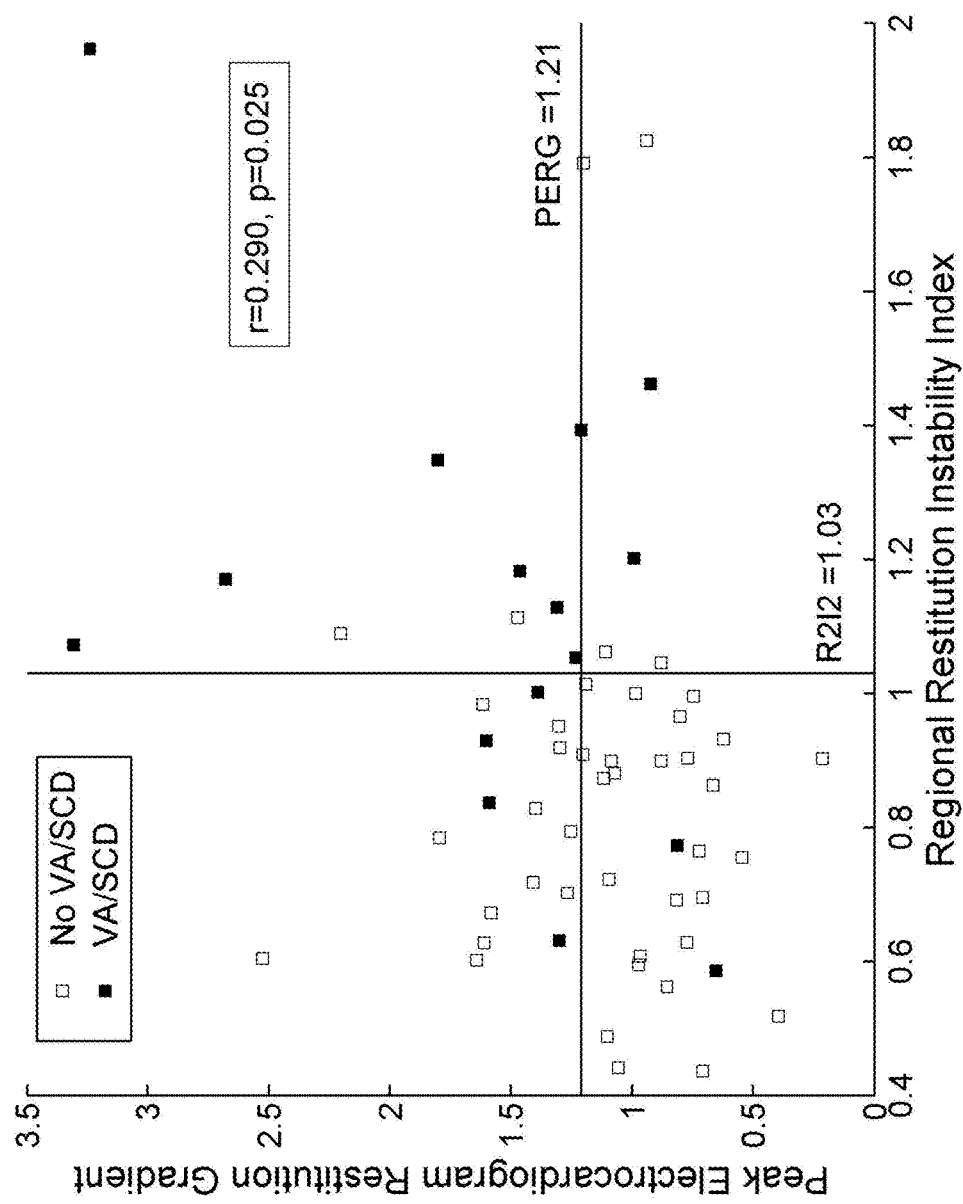

FIG. 20 shows a plot of Regional Restitution Instability Index against Peak ECG Restitution gradient. Lines are drawn at the pre-selected cut-off value for R2I2 and at the optimal cut-off of 1.21 for PERG. Spearman rank correlation analysis minimal correlation between 12 lead mean peak restitution gradient and R2I2 (r=0.290, p=0.025).

Figure 21:
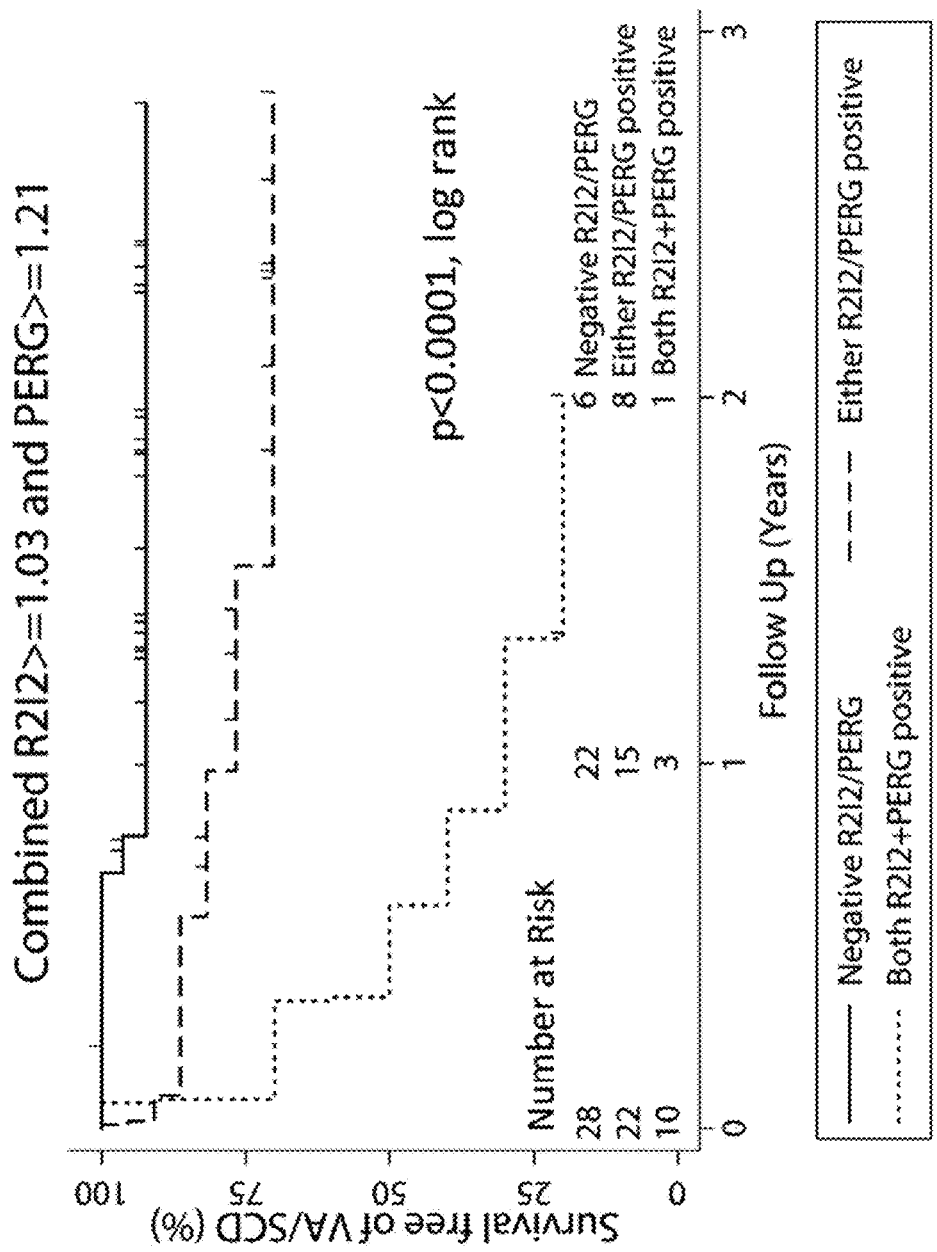

FIG. 21 shows a Kaplan Meier curve showing significant separation of the curves for survival free of ventricular arrhythmia/sudden cardiac death for patients partitioned by: both R2I2<1.03 and PERG<1.21/either R2I2≥1.03 or PERG≥1.21/both value R2I2≥1.03 and PERG≥1.21 (p<0.0001, log rank).

1. EXAMPLE 1: INCLUSION CRITERIA

Patients being considered for new ICD implantation with NYHA class II-III symptoms of heart failure and documented left ventricular dysfunction.

2. EXAMPLE: EXCLUSION CRITERIA

Unstable coronary heart disease, likely to need percutaneous or surgical intervention
Requirement for constant cardiac pacing (such as high grade AV block or for cardiac resynchronisation)
Recent coronary artery bypass graft surgery (within 3 months)
Recent valvular surgery (within 3 months)
Recent myocardial infarction (as documented by appropriate ECG & biochemical analysis) (within 3 months)
2.1 Primary Outcome Measure: ICD Therapy for Ventricular Arrhythmia or Death within a 2 Year Follow Up Period

3. EXAMPLE 3: STUDY PRACTICED ON PATIENTS INCLUDED AFTER ANALYSIS FROM EXAMPLES 1 AND 2

A) Subjects were separated into two groups (the first group being patients determined to at high risk of cardiac arrhythmia; the second group being patients determined to be at low risk of cardiac arrhythmia) studied in the post absorptive state.
B) Appropriate aseptic technique employed throughout.
C) Cutaneous ECG leads were applied in the standard positions and connected to an appropriate electrophysiological recorder. (Bard system used for study standard 12 lead ECG positions)
D) An appropriate transvenous route was selected and the Seldinger technique employed to insert a 6F venous sheath.
E) An appropriate electrophysiology catheter, for example the 6F Josephson Quadripolar catheter, was inserted through the sheath.
F) Fluoroscopic guidance was used to manipulate the catheter into the right ventricular apex, where a stable position was obtained.
G) The ventricular stimulation threshold was obtained, preferably via the diastolic approach.
H) An appropriate pacing protocol was delivered with rectangular pulses of 2 ms duration set sufficiently greater than the threshold to achieve reliable stimulation with a preferred value of 3 times the diastolic threshold. The pacing protocol used was the same for each patient in the study.

Figure 1A:
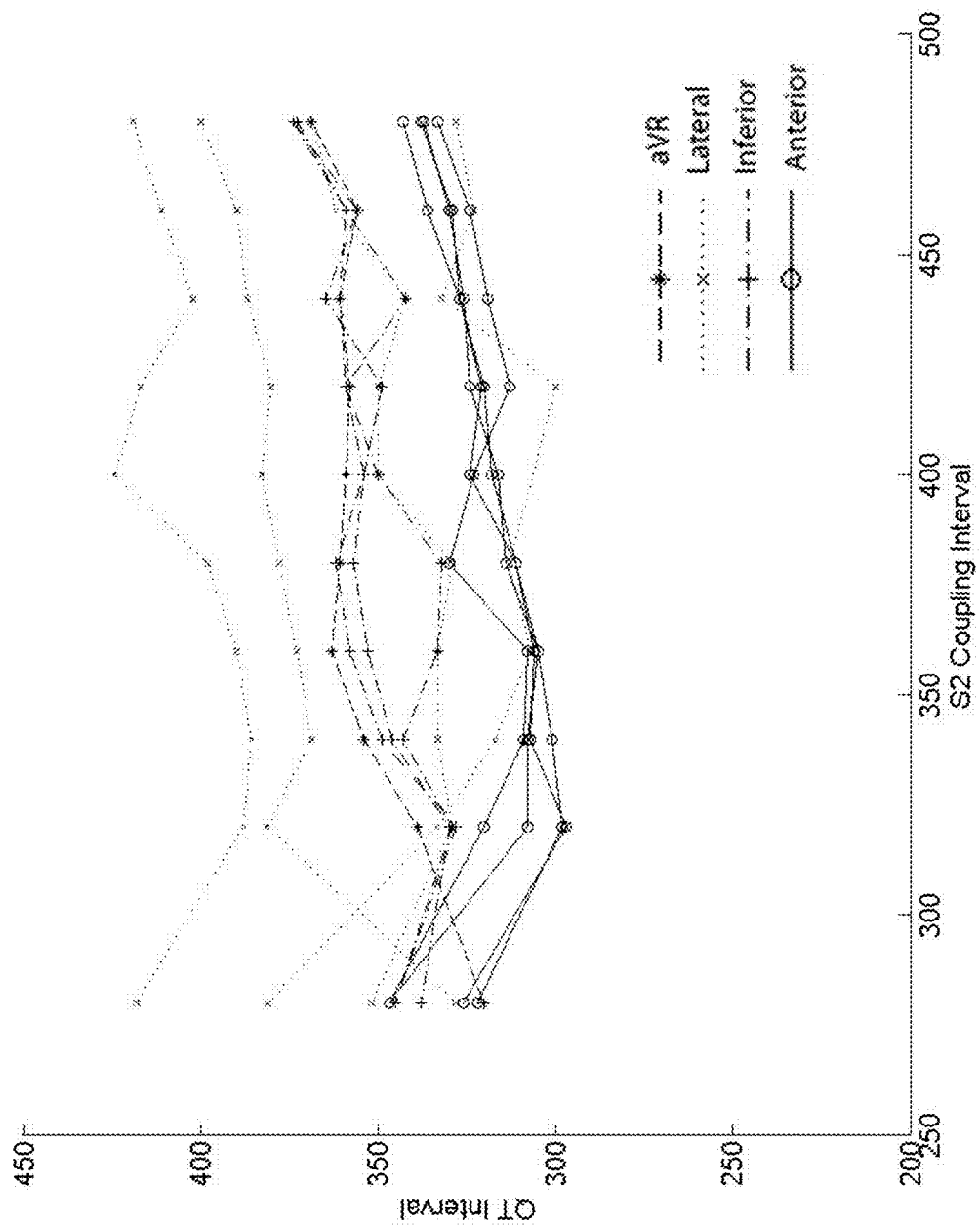
FIG. 1a shows a cutaneous APD restitution graph from a subject suffering from arrhythmia.
Figure 1B:
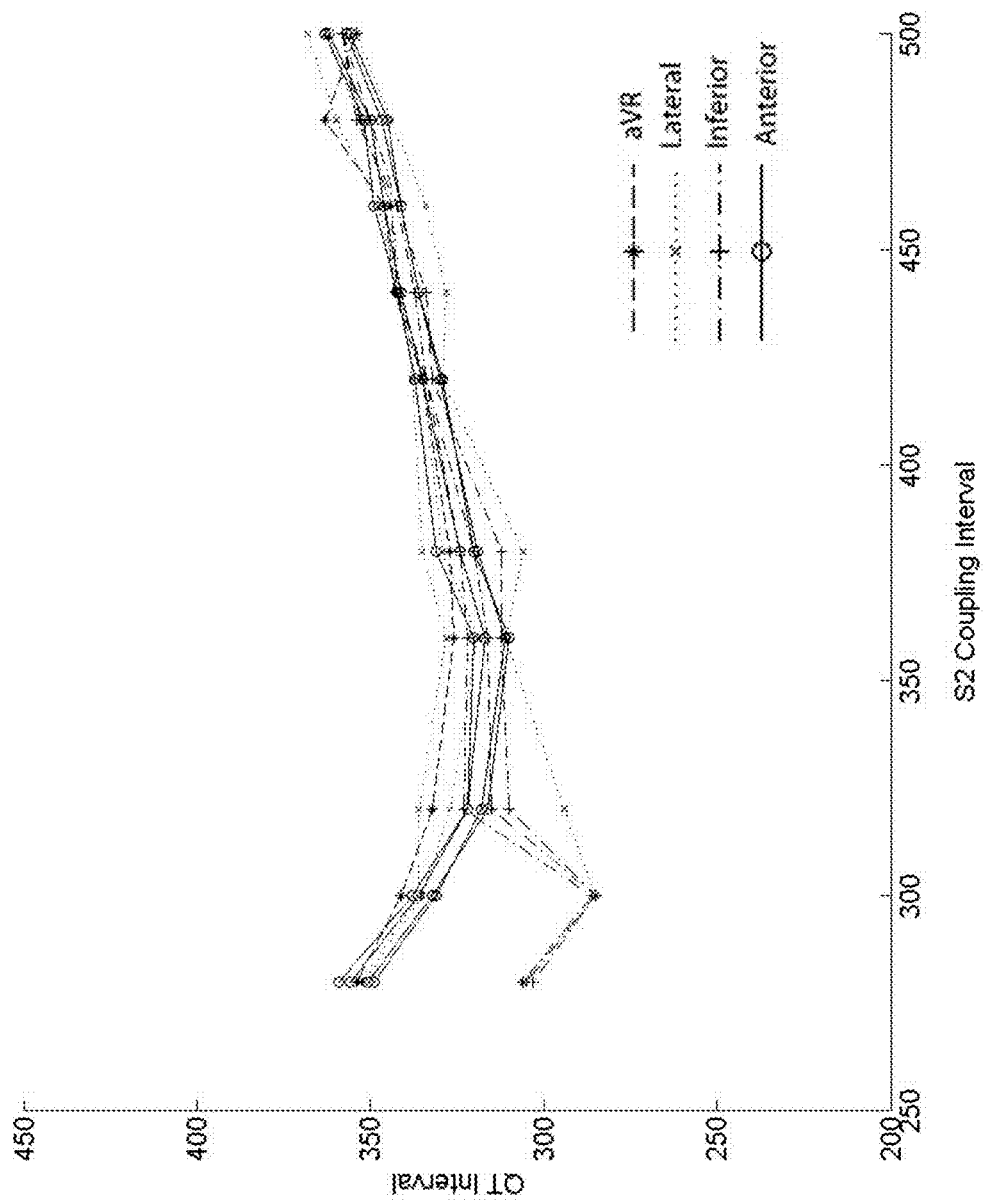
FIG. 1b shows a cutaneous APD restitution graph from a subject that does not suffer from arrhythmia.
Figure 2A:
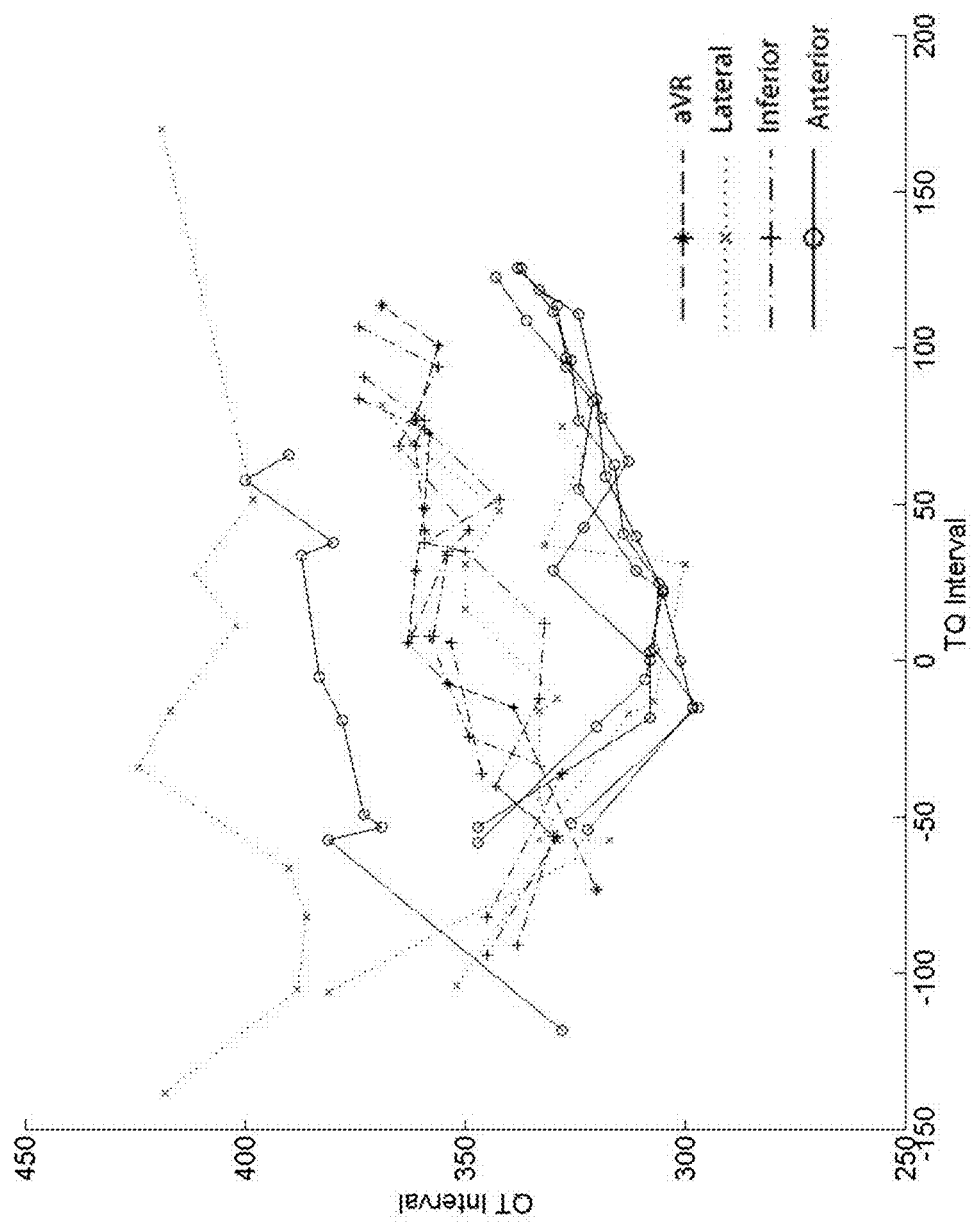
FIG. 2a shows a continuous cutaneous APD restitution graph from a subject suffering from arrhythmia.
Figure 2B:
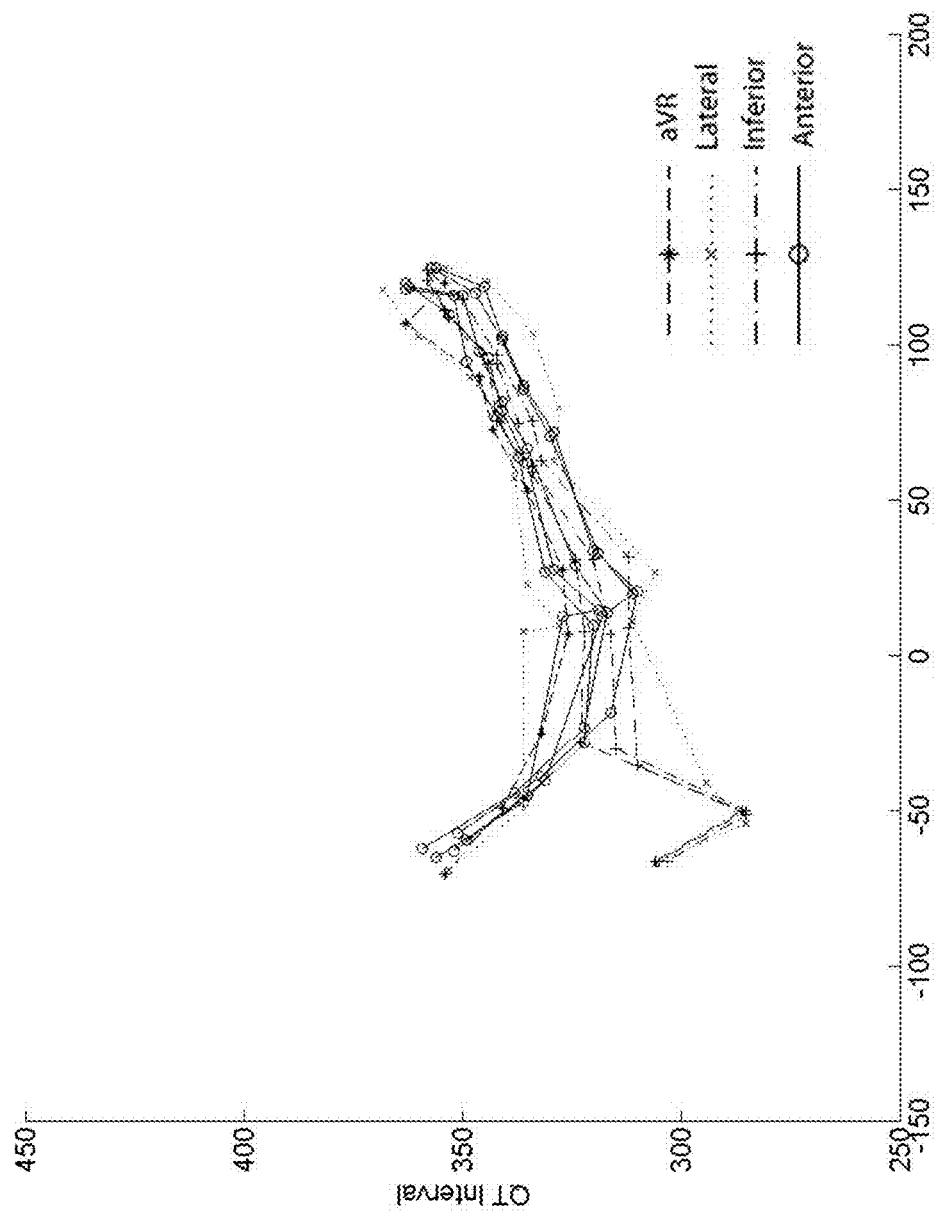
FIG. 2b shows a cutaneous APD restitution graph from a subject that does not suffer from arrhythmia.
Figure 3:
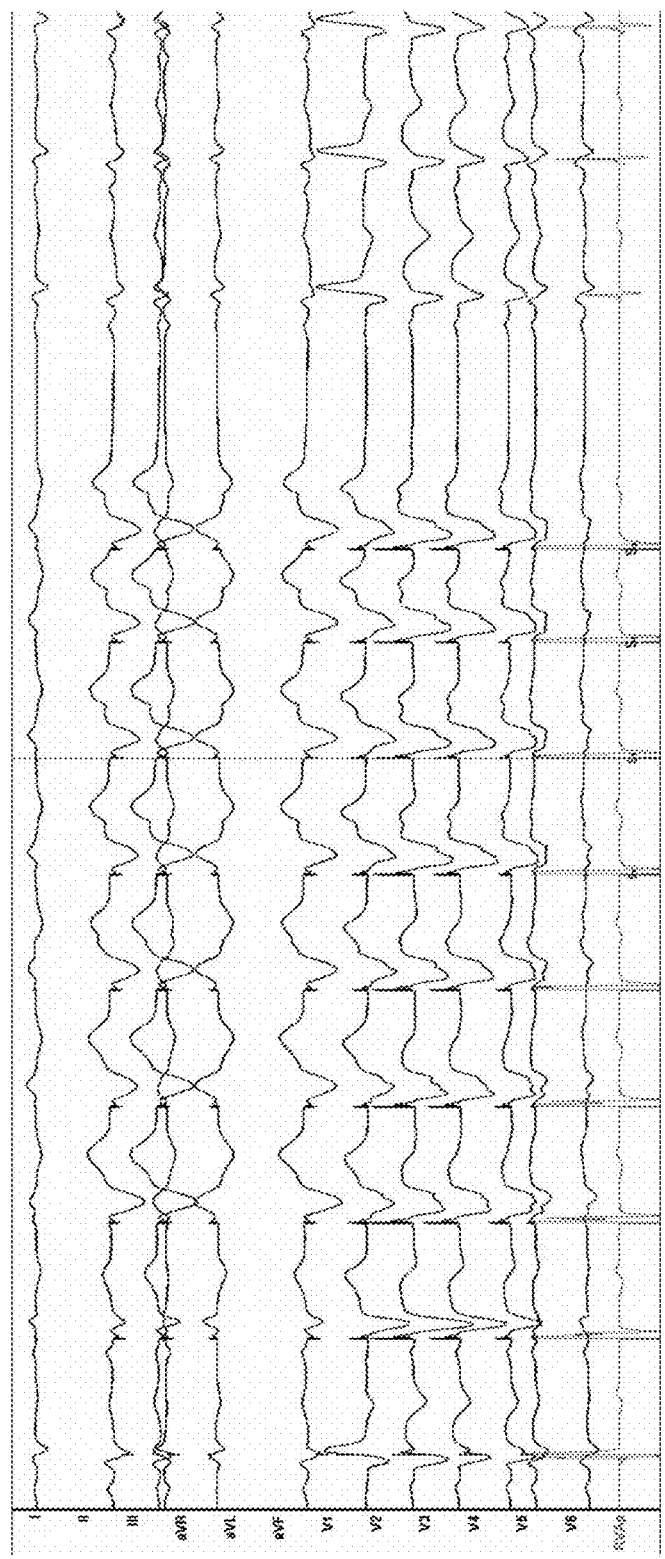
FIG. 3 shows analog digitized and recorded at 1000 Hz with 12-bit resolution data from ECG (expanded from portion of that shown in FIG. 4).
Figure 4:
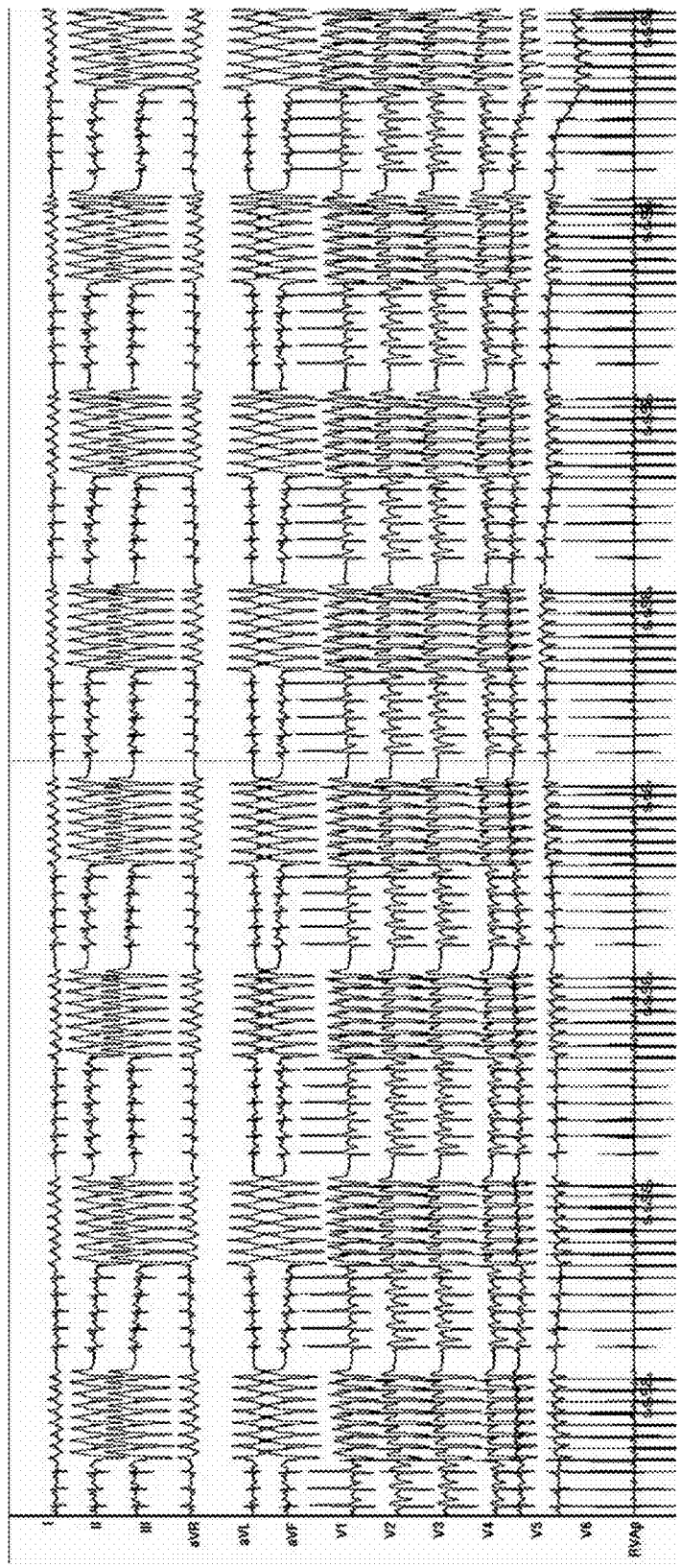
FIG. 4 shows analog digitized and recorded at 1000 Hz with 12-bit resolution data from ECG.

I) Analog data were digitized and recorded at 1000 Hz with 12-bit resolution, shown in FIGS. 3 and 4. Low pass filter was set to 50 Hz and high pass filter set to 0.01 Hz.
J) Data analysis was performed with custom-written analysis programs in the MATLAB 2009a language.
K) For consistency QT measurements were taken as from the start of the pacing spike to the peak of the T wave and TQ measurements were taken as from the peak of the T wave to the start of the pacing spike.
L) The QT/TQ restitution graphs were determined by plotting QT as a function of preceding TQ and by plotting QT as a function of S2 coupling interval (see FIGS. 1a, 1b, 2a and 2b).

4. EXAMPLE 4: PILOT STUDY EXPLORING THE REGIONAL REPOLARISATION INSTABILITY INDEX IN RELATION TO MYOCARDIAL HETEROGENEITY AND PREDICTION OF VENTRICULAR ARRHYTHMIA AND DEATH 4.1 Methods
4.1.1. Subjects were identified by screening the department audit databases for patients with a history of IHD who had undergone programmed electrical stimulation (PES) between 1 Jan. 2005 and 31 Jul. 2009 as part of clinical risk stratification for ICD implantation and who had had a CMR scan within 6 months of their PES. This identified 43 patients. PES recordings were unavailable for 9 patients and 4 more patients were excluded because only 6 lead ECGs had been recorded. Of the 30 patients whose PES data were available 1 could not be analysed because their drive cycle length (DCL) was changed midway through the protocol. CMR data was then sought for these 30 patients. LGE images were not acquired for 3 patients because of difficulties gating (1) and breath holding (2) and 4 patients could not be analysed because of an incompatibility between the acquisition and peri-infarct zone analysis software. LGE CMR images were available for 23/30 patients.
4.2 Electrophysiological Study
4.2.1. Studies were performed as per the standard departmental protocol which did not change for the duration of the study. Fasting subjects were studied with minimal sedation and with antiarrhythmic drug cessation 4-5 half-lives prior to the procedure. A 6F Josephson quadripolar catheter was advanced transvenously first to the right ventricular apex (RVA) and then the right ventricular outflow tract (RVOT). Electrocardiograms were recorded using LabSystem Pro (BARD, Lowell) at 1 kHz sampling rate with a low pass filter set to 50 Hz and high pass filter set to 0.01 Hz. The ventricular stimulation test followed a modified Wellens protocol with two 8 beat drive trains at the RVA with drive cycle length (DCL) 600 ms and 400 ms and one 8 beat RVOT drive train with DCL 400 ms. If breakthrough beats were seen in the drive train the DCL was reduced. Up to 3 extrastimuli were used with each drive train; the extrastimulus was typically started at 500/360 ms and reduced in 20 ms steps. Monomorphic VT of duration greater than 30 seconds or associated with haemodynamic compromise was recorded as positive; the test was otherwise recorded as negative. The S1 S2 coupling interval is the period between the last beat of the drive train and the first extrastimulus, this part of the PES was used to derive the R2I2.
4.3 Analysis of the R2I2
4.3.1. The electrocardiograms were exported at 16-bit digital resolution for analysis in bespoke software written in MatLab (Mathworks, Natick). The timing of the QRS onset (QRSo) and T wave peak (Tp) were analysed automatically and all data points were manually verified, a senior electrophysiology research fellow blinded to the CMR data, the PES result and endpoint data. The Tp was chosen in preference to the end of the T wave (Te) because of the known difficulties in measuring Te.

Intra and inter-operator reproducibility (8 cardiology specialists mean 10.1 years of cardiology training) were assessed using a representative sample of 48 paced ECG points from the dataset. Mean intra-operator variability for measurement of the QRSo and Tp was 6.3 ms (SD 16.3 ms) vs. inter-operator 6.4 ms (SD 16.7 ms).
4.3.2. Data points were censored according to predetermined rules: 1. Breakthrough beat occurring after beat 6 of the drive train (51/316 drive trains censored), 2. Point indeterminate due to artefact, baseline wander or unclear morphology (256/3089 points censored). For each 51 S2 coupling interval the DI was taken as the period from Tp on the last beat of the DCL to the S2 QRSo as detailed in FIG. 5 and is referred to as the TpQ interval, note the possibility for negative TpQ as measured in this way. The cutaneous surrogate for the APD was taken as the period from S2 QRSo to the S2 Tp (QTp). The TpQ interval and QTp were measured at each S2 performed at the RVA; where possible the DCL 600 ms drive train was used but if it was not present or unusable due to breakthrough beats an alternative DCL was selected.
4.3.3. FIG. 6 shows a representative plot of the dynamic relationship of TQ interval and QT interval for a number of lead types. The focus of the study was on regional electrical heterogeneity and as such the ECG leads were divided into regions based on anterior (V1-4), inferior (II,III,aVF) and lateral (I,aVL,V5,V6) leads. For each lead QTp was plotted as a function of TpQ, points were then grouped by ECG region and S1 S2 coupling interval and for each lead the mean of the squared residuals from best fit points was recorded (FIG. 11). This number was then expressed as a proportion of the mean value for each lead across all patients to account for differences in lead distribution. The mean of the maximum regional values was taken as the R2I2 and investigated as a marker of VA or death. FIGS. 7 to 10 illustrate further how this analysis is calculated, with Table 3 providing the final analysis of the study shown in FIGS. 7 and 10 where normalised values of the results are calculated.
4.4. Late Gadolinium Enhanced Cardiac Magnetic Resonance Imaging Protocol
4.4.1. Patients underwent LGE CMR as per departmental protocol within 63±63 days of their PES study (in all but one patient the CMR was performed before the PES study) as per the retrospective criteria used to select patients. Comprehensive CMR imaging was performed using a 1.5-T scanner (Siemens Magnetom, Avanto) with ECG triggering and a 6 channel phased array cardiac coil. After scout imaging, steady-state free precession (TrueFISP) cine images were acquired in 4, 3 and 2 chamber-views and a series of short axis slices were obtained using SSFP cine imaging covering the LV from base to apex, with 1 slice every 10 mm. A gadolinium-based contrast agent (0.1-0.2 mmol/kg) was administered intravenously as a bolus and (LGE) images were obtained approximately 10 minutes later with the use of an inversion-recovery, segmented gradient echo sequence.
4.5. CMR Analysis
4.5.1. All analysis was performed offline blinded to patient details using commercially available software. Volumetric analysis was performed by manual tracing of endocardial and epicardial contours; LV end-diastolic volume (LVEDV), end-systolic volume (LVESV), stroke volume (SV), LV ejection fraction (LVEF) and LV end-diastolic mass (LVM) were calculated. LGE images were analysed for scar and PIZ mass using a modification of the Schmidt et al technique. All voxels with signal intensity greater than 50% of peak infarct core were recorded as scar. PIZ was defined as all pixels in the region of the MI with signal intensity >2 standard deviations (SD) above mean intensity in an area of normal myocardium and below 50% of the peak intensity (FIG. 12). CMR volumes and mass were indexed to height. Scar size is presented as % of LV mass and PIZ as mass in grams, % of LV mass and % of infarct size.

4.6. Statistical Analysis 4.6.1. The primary endpoint was time to VA or death. Parametric data are expressed as mean±standard deviation (SD) and analysed using Student's t-test; non-parametric data as median [inter-quartile range] (IQR) and analysed using Mann-Whitney U test; proportions were analysed using a one sided Fisher's exact test. The population R2I2 median value was used to separate "high risk" and "low risk" results for the R2I2 and a Kaplan-Meier survival curve was drawn for R2I2>median vs. R2I2≤median with comparison of cumulative VA/death based on logarithmic transformations. Pearson rank correlation was used to look for correlation between the R2I2 and PIZ. A single Cox proportional hazards model was used to look for independence of the R2I2>median, PES result, LVEF and QRS duration (QRSD). A p-value <0.05 was considered statistically significant. All analyses were performed using STATA (StataCorp LP, College Station).

4.7. Results 4.7.1. The clinical characteristics, R2I2 and PIZ data for the 30 patients are summarised in Table 1. R2I2 data and CMR volumetric analysis, were available for 29 of the patients and LGE CMR data were available for 23, both were available for 22 patients. R2I2max3 and R2I2maxRdata for each patient can be found in Table 2. R2I2max3 being a measurement based on analysis of TpQ and QTp and calculated as the mean of the maximum regional normalised mean values. R2I2maxR being a measurement based on analysis of TpS and JTe and calculated as the largest normalised mean value. Fourteen patients had a positive PES of whom 13 had ICD implantation, no patients with negative PES had ICD implantation during the study follow up period. Median follow up duration was 725 days (IQR 553 days). Seven patients reached the primary endpoint of VA/death during follow up, 4 VA and 4 deaths (1 patient had successful ICD therapy for VA and subsequently died). Survival was recorded as time to first endpoint/the end of follow up.

4.7.2. When data was analysed using the population median R2I2max3value, patients with R2I2>median have a significantly higher VA/death rate than those with R2I2 median (6/14 vs. 1/15 p=0.031). Kaplan-Meier survival curves for the 2 groups are shown in FIG. 13, with the populations diverging significantly (p=0.017, log rank test). As would be expected age and PES result were close to being significantly related to outcome but were not correlated with R2I2. The extent of PIZ showed a trend towards an association with VA/death (13.59, IQR 8.51 vs. 7.51, IQR 8.39, p=0.093) and modest correlation with the R2I2 (r=0.41 p=0.057), FIG. 14. Cox multivariate analysis of R2I2 median, PES result, LVEF and QRSD showed that R2I2 median was an independent predictor of VA/death (p=0.032). Kaplan-Meier survival curves for the same group analysed as R2I2maxR are shown in FIG. 16.

TABLE 1

| Variable | Whole group (n = 30) | No VA/Death (n = 23) | VA/Death (n = 7) | P |
|---|---|---|---|---|
| Age (years) | 67 ± 9 | 65 ± 9 | 72 ± 8 | 0.055 |
| Sex (% male) | 97 | 96 | 100 | ... |
| DCL (ms) | 23 × 600, 1 × 550, 5 × 400 | 16 × 600, 1 × 550, 5 × 400 | All 600 | ... |
| QRSD (ms) | 107 ± 20 | 107 ± 21 | 106 ± 15 | 0.95 |
| LVEF (%) | 31 ± 14 | 32.4 ± 15 | 27 ± 7.5 | 0.34 |
| PES result (positive/total) | 12/30 | 7/23 | 5/7 | 0.068 |
| R2I2 | 1.38 [0.88] | 1.22 [0.90] | 1.76 [0.58] | 0.075 |
| R2I2 > median (positive/total) | 14/29 | 8/22 | 6/7 | 0.031 |
| EDV index (ml/cm) | 1.48 ± 0.41 | 1.49 ± 0.41 | 1.45 ± 0.45 | 0.84 |
| SV index (ml/cm) | 0.42 ± 0.14 | 0.43 ± 0.14 | 0.39 ± 0.15 | 0.47 |
| Mass index(gm/cm) | 0.78 ± 0.17 | 0.75 ± 0.23 | 0.77 ± 0.15 | 0.81 |
| Height (cm) | 170 ± 7 | 169 ± 8 | 173 ± 5 | 0.24 |
| Follow up (months) | 24 [18] | 24 [16] | 16 [16] | 0.088 |
| PIZ % | 7.8 [10.7] | 7.5 [8.4] | 13.6 [8.5] | 0.093 |
| PIZ mass (gm) | 10.3 [15.8] | 7.8 [9.7] | 16.7 [12.8] | 0.161 |
| PIZ mass/Scar Mass | 0.67 [0.66] | 0.67 [0.64] | 0.67 [0.53] | 0.78 |
| Scar % | 10.9 [16.5] | 9.67 [13.5] | 21.9 [17.8] | 0.16 |

TABLE 2

| Dead/AT | Time to Death/AT | R2I2max3 | R2I2maxR |
|---|---|---|---|
| 1 | 492 | 1.5713 | 1.3815 |
| 1 | 1046 | 2.0153 | 1.4117 |
| 1 | 122 | 1.1857 | 1.0557 |
| 1 | 384 | 1.436 | 2.3839 |
| 1 | 865 | 1.8388 | 2.4571 |
| 1 | 631 | 1.7603 | 1.208 |
| 1 | 502 | 4.3956 | 2.5317 |
| 0 | 361 | 1.144 | 0.9638 |
| 0 | 601 | 1.0352 | 0.5599 |
| 0 | 1456 | 1.0228 | 1.0991 |
| 0 | 795 | 0.7533 | 0.5867 |
| 0 | 1376 | 1.0829 | 1.2713 |
| 0 | 655 | 2.3692 | 0.9575 |
| 0 | 1247 | 1.0118 | 1.0043 |
| 0 | 578 | 2.2275 | 2.6992 |
| 0 | 874 | 0.379 | 0.6112 |
| 0 | 473 | 3.842 | 4.3457 |
| 0 | 1069 | 0.9167 | 0.8627 |
| 0 | 742 | 1.3929 | 2.6172 |
| 0 | 522 | 1.0024 | 0.324 |
| 0 | 1054 | 1.3069 | 1.1769 |
| 0 | 1306 | 1.3781 | 0.7677 |
| 0 | 732 | 1.6938 | 2.502 |
| 0 | 942 | 0.8577 | 2.4208 |
| 0 | 718 | 1.9053 | 1.9395 |
| 0 | 1350 | 2.9189 | 1.2323 |
| 0 | 354 | 0.5353 | 12.0136 |
| 0 | 391 | 3.3542 | 0.5685 |
| 0 | 624 | 1.2884 | 0.9892 |

TABLE 3

|  | Anterior | | | | Lateral | | | | Inferior | | |
| --- | --- | --- | --- | --- | --- | --- | --- | --- | --- | --- | --- |
|  | V1 | V2 | V3 | V4 | I | avL | V5 | V6 | II | III | avF |
| Patient x Mean | 749 | 181 | 98 | 111 | 3330 | 1603 | 600 | 1912 | 44 | 58 | 67 |
| Population Mean | 596 | 279 | 357 | 848 | 1440 | 875 | 1383 | 1846 | 180 | 132 | 72 |
| Normalised values for patient x | 1.3 | 0.6 | 0.3 | 0.1 | 2.3 | 1.8 | 0.4 | 1.0 | 0.2 | 0.4 | 0.9 |

4.8. Discussion 4.8.1. This pilot investigation suggests that R2I2 may be a useful prognostic marker stratifier in patients with IHD at risk of SCD. Patients with ischaemic cardiomyopathy who subsequently had a VA or died had higher R2I2 than those without an event. The R2I2 electrical measure of risk shows a moderately strong correlation with an anatomic measure of arrhythmic substrate, the extent of PIZ. Conceptually the R2I2 has superficial similarities to QTp dispersion as both involve measurement of inter-lead differences in the QTp interval duration. The R2I2 has been developed with the weaknesses of QTp dispersion in mind. Firstly it is a dynamic measure: as the S1 S2 coupling interval shortens the complex interplay of restitution and anatomical factors will influence the QRS and T loops, the ECG resulting from this will in part reflect the projection of the changing QRS and T loops but the effects of this are likely to be separate from the changes due to repolarisation heterogeneity. FIG. 15 shows an example of 12 regional differences in repolarisation developing as the S1 S2 coupling interval shortens in a patient who went on to develop VA. Secondly the R2I2 is based on regional QTp variation and is designed to minimise influence by the baseline QTp dispersion. Thirdly the R2I2 measurements are made from paced ECGs and the T wave peak has been used for optimal reproducibility.

Abbreviations

| CMR | Cardiac magnetic resonance |
| --- | --- |
| CV | Conduction velocity |
| DCL | Drive cycle length |
| DI | Diastolic interval |
| ECG | Electrocardiogram |
| EP | Electrophysiological |
| ICD | Implantable cardioverter defibrillator |
| IHD | Ischaemic heart disease |
| IQR | Inter-quartile range |
| JTe | J point to end of the T wave |
| LGE | Late gadolinium enhancement |
| LVEDV | Left ventricular end-diastolic volume |
| LVEF | Left ventricular ejection fraction |
| LVESV | Left ventricular end-systolic volume |
| LVM | Left ventricular end-diastolic mass |
| MI | Myocardial infarction |
| PES | Programmed electrical stimulation |
| PIZ | Peri-infarct-zone |
| QRSo | QRS onset |
| R2I2 | Regional repolarisation instability index |
| RVA | right ventricular apex |
| RVOT | Right ventricular outflow tract |
| SCD | Sudden cardiac death |
| SD | Standard deviation |
| SI | Signal intensity |
| SV | Stroke volume |
| Te | End of the T wave |
| Tp | T wave peak |
| TpS | T wave peak to pacing spike |
| VA | Ventricular arrhythmia |

5. PERG METHODS

Study population and Protocol

This was a prospective, single centre study that enrolled 62 consecutive patients with ischaemic cardiomyopathy (ICM) between January 2010 and March 2012. The study was blinded in that analysis of electrical data on all subjects was performed prior to ascertaining the endpoint of VA/SCD. Inclusion criteria were patients over age 18 referred for ICD implantation or SCD risk stratification with programmed electrical stimulation. Exclusion criteria were: indication for cardiac resynchronisation therapy, less than 28 days since an acute coronary syndrome/cardiac surgery, pregnancy, unable to give informed consent and contraindication to electrophysiological study (e.g. haemodynamic instability). Ethical approval was granted by the Derbyshire Research Ethics Committee (09/H0401/70) and the study protocol was approved by the Research and Development Office of the University Hospitals of Leicester National Health Service Trust (UHL-10824) (Leicester, UK). All patients gave written, informed consent. Following recruitment, two patients were excluded: 1 patient did not have electrophysiology data collected because he declined ICD implant after recruitment (electrophysiology data was typically acquired during ICD implant) and 1 patient's electrophysiological data were corrupted and not analysable. The primary endpoint was ventricular arrhythmia/sudden cardiac death (VA/SCD). Ventricular arrhythmia was taken to be ventricular fibrillation or ventricular tachycardia of duration greater than 30 seconds or terminated appropriately by ICD shock/antitachycardia pacing. For the purposes of this study the ACC/AHA/ESC 2006 definition for SCD was taken: "death from an unexpected circulatory arrest, usually due to a cardiac arrhythmia occurring within an hour of the onset of symptoms". (12) Endpoints were assigned by a three member independent committee with access to clinical records. 8

Electrophysiological Study

Fasting subjects were studied with minimal sedation. The Electrophysiological study (EPS) protocol was performed with programmed electrical stimulation at the RV apex through either a 6F quadripolar catheter (St Jude Medical, Minnesota, USA) or a 65 cm 7F Durata ICD lead (St Jude Medical, Minnesota, USA). Standard 12 lead ECG was recorded with signals recorded at 1 kHz sampling rate with a low pass filter set to 50 Hz and high pass filter set to 0.01 Hz. Bipolar or unipolar stimulation protocols were delivered through either the proximal two poles of the quadripolar catheter or using the proximal pole of the ICD lead respectively. Rectangular pulses of 2 ms duration at 3 times the diastolic threshold were delivered according to the following protocol. A 10 beat train at drive cycle lengths of 600 ms and 400 ms followed by a single extrastimulus at 500/360 ms with decrements of 20 ms to 300 ms and 10 ms to effective refractory period. If breakthrough beats were seen in the drive train the drive cycle length was reduced to 500 ms and the extrastimulus started at 460 ms. The S1-S2 coupling interval is the period between the last beat of the drive train and the first extrastimulus, the R2I2 was derived from measurements taken from the last S1 and the S2 beats. Programmed electrical stimulation was performed using a modified Wellens protocol at the right ventricular apex (two drive trains, drive cycle length 600 ms and 400 ms, up to 3 extrastimuli). (13) Monomorphic ventricular tachycardia of duration greater than 30 seconds or associated with haemodynamic compromise was recorded as positive; the test was otherwise recorded as negative. It was necessary to delay the EPS in 7 patients due to anticoagulation requirement; these patients had the same protocols as detailed above delivered through their ICD with bipolar pacing set as close to three times the diastolic threshold as the programmer allowed. 9
Analysis of the R2I2

The surface electrocardiograms were exported at 16-bit digital resolution for analysis in custom software written in MATLAB version R2009a (Mathworks, Natick, USA) by WBN with further work to refine the software by Madeiro et al. (14) The timing of the QRS onset, T wave peak (Tp) and T wave end (Te) were analysed automatically and all data points were manually verified by WBN. The R2I2 is derived using ECG surrogates for the APD (i.e. QRS onset to T wave peak (QTp) and DI (i.e. T wave peak to QRS onset (TpQ)). Published R2I2 analysis has used QTp/TpQ and this was used as our primary measure with additional assessment made of QRS onset to T wave end (QTe)/T wave end to QRS onset ((TeQ) (QTe/TeQ) to see if this provided equivalent or better discrimination (FIG. 17A and see below). For each lead of the ECG the APD surrogate was plotted as a function of DI surrogate and gradients were fitted using 40 ms overlapping least squares linear segments as described previously by Taggart et al. (FIG. 17B). (15) The difference of the gradient from the mean gradient was calculated across the ECG leads in each 40 ms segment. The standard deviation of these values within each ECG lead was taken as a measure of APD heterogeneity in each lead. The mean of this was then taken as the R2I2 (no units). (11) A fully worked example of the R2I2 calculation is shown in the supplementary file. Data points were censored out according to predetermined rules: 1. Breakthrough beat occurring after beat 8 of the drive train or a repetitive ventricular response beat interfering with measurement of the Tp/Te (73/859 drive train beats censored), 2. Point indeterminate due to low amplitude T wave, low signal to noise ratio, baseline wander, artefact or unclear morphology (340/9432 points). A small number of non-physiologically steep gradients result from points that have near or identical TpQ (measured to the nearest millisecond). To avoid skewing of the data, gradients exceeding ±10 were censored out, 1.6% (198/12511) of gradients were censored out. For 10 consistency in comparison between Tp and Te the same dataset was used for both fiducial points: ECG complexes in which both Tp and Te were measureable were analysed Intra-observer and inter-operator variability of R2I2 was assessed using a representative sample of 5 patients from the dataset (856 QTp and TpQ intervals) and was performed independently by two electrophysiology research fellows (WBN and MIS). The intra-class correlation coefficient was 0.86 and 0.93 respectively for intra-observer and inter-observer agreement (p<0.05). Intra-observer variability of TpQ values was mean−1.2 ms (standard deviation 5.5 ms) compared with inter-operator mean 2.8 ms (standard deviation 6.1 ms); Intra-observer variability of QTp values was mean−0.9 ms (standard deviation 6.0 ms) compared with inter-operator mean−2.6 ms (standard deviation 6.7 ms). Choice of Electrocardiogram Surrogate for Action Potential Duration Electrocardiogram surrogates for APD/DI are used in the R2I2 calculation. To date R2I2 research has favoured use of QTp/TpQ over the more natural choice of QTe/TeQ because of known challenges in accurate, reproducible identification of Te. (16) There is no definitive ECG surrogate for the APD/DI but there is a strong theoretical basis, although with conflicting viewpoints, to suggest that the TpTe portion of the QTe interval reflects dispersion of repolarisation. (17,18) It could be argued that QTe is more reflective of APD and therefore might improve R2I2. Substituting QTe/TeQ for QTp/TpQ in the R2I2 calculation did not discriminate VA/SCD endpoints and did not appear to offer additional value to standard R2I2. 11
Calculation of Peak Electrocardiogram Restitution Gradient The mean gradient at each S1-S2 coupling interval was calculated across the 12 ECG leads from the gradients used in the R2I2 and the peak value was then taken as the PERG. Example QTp/TpQ plots for patients with low and high R2I2 and low and high PERG are given in FIG. 18. In each of these examples 12 lines are plotted, each connects the QTp/TpQ points for one ECG lead. This allows differentiation of the different ECG leads and is visually clearer than a plot containing all of the gradients (an example of a gradient plot is given in the supplementary file). The timing of Tp varies across the 12 ECG leads and this results in TpQ and QTp offsetting of the different ECG leads, this effect is best seen with the lateral leads (lead I particularly) in FIGS. 18A and C. In patients with low R2I2 (FIGS. 18C and D) the ECG leads run relatively parallel courses compared to patients with high R2I2 (FIGS. 18A and B) whose ECG leads follow inharmonious, erratic courses. In patients with high PERG (FIGS. 18A and C) the gradient steepens at shorter TpQ intervals compared with patients with low PERG (FIGS. 18B and D) who have more horizontal ECG lead paths with little decrease in QTp at shorter TpQ intervals.
Sample Size and Statistical Analysis The sample size was informed by a two sample t-test power calculation using the Satterthwaite approximation for unequal variances and using R2I2 data from our previous retrospective study (R2I2 in VA/death group compared with No VA/death group (mean±SD: 1.30±0.25 versus 1.03±0.27)). (11) To achieve 80% power at a 5% significance level, to show that R2I2 was significantly higher in ICM patients reaching the endpoint of VA/SCD versus those not, required 10 patients reaching endpoint. Audit of our ICD service found a rate of appropriate ICD therapy of 15% per year. Therefore to achieve sufficient events (>10 events) in a 12-18 month period, a sample size of ~60 patients was determined. 12

Parametric data are expressed as mean±SEM and analysed using Student's t-test; non-parametric data as median [inter-quartile range] and analysed using the Mann-Whitney U test. Proportions were analysed using a two-sided Fisher's exact test. A receiver operator characteristic curve using the R2I2 was constructed in the study cohort and the area under the curve calculated. The retrospective study of R2I2 has previously found a cut-off R2I2 value of 1.03 provided the best discrimination of endpoint versus not reaching endpoint. (11) An optimal peak ECG restitution gradient (PERG) cut-off of 1.21 was selected to partition patients into "high" and "low" risk groups. Kaplan-Meier survival curves were drawn for patient sub-groups partitioned by this R2I2 cut-off and for patient sub-groups partitioned by combinations of R2I2 and PERG cut-offs; comparison of cumulative endpoints was based on logarithmic transformations. Survival was recorded as time to first endpoint or the end of follow up. Piecewise Poisson models were used to estimate an incidence rate ratio (IRR, equivalent of hazard ratio) for the R2I2≥1.03/PERG≥1.21 and to assess independence of R2I2≥1.03/PERG≥1.21 from programmed electrical stimulation result, left ventricular ejection fraction and QRS duration in the study group. A Piecewise Poisson model was also used to compare and assess independence of standard R2I2≥1.03 with PERG≥1.21. The Piecewise Poisson model is a generalised linear model and is equivalent to a Cox proportional hazards model but allows control of time dependant effects due to non-proportional hazards. Analysis was performed across the whole time frame splitting the data at 9 months and then averaging the estimates for each time period using the inverse variance as weights. For R2I2 using QTe/TeQ the median value was used to partition patients into "high" and "low" risk groups. Pearson rank correlation was used to look for correlation between parametric data and Spearman rank correlation was used for non-parametric data. Intra-observer 13 and inter-observer agreement for the R2I2 was calculated using the intra-class correlation coefficient for absolute agreement. A p-value <0.05 was considered statistically significant. All analyses were performed using STATA version 11 (StataCorp LP, College Station, USA).

Results

Regional Restitution Instability Index

Median follow up was 22 months (range 3-34 months) during which 16 patients reached the endpoint of VA/SCD, 15 patients had VA and 2 patients had SCD (1 patient had VA and SCD). Other deaths, not counted as endpoints, were due to: 1 ruptured aortic aneurysm, 1 heart failure and 1 ventricular tachycardia storm (counted as VA, this patient had VA prior to the terminal admission). ICDs were fitted in 51/60 patients; there were no endpoints reached in patients who did not have ICDs fitted.

Patient characteristics partitioned on the basis of the primary endpoint are shown in Table 1. Patients who reached the endpoint were more likely to have a secondary prevention ICD indication (p=0.04) but had otherwise similar clinical characteristics to those not reaching endpoint. Patients that reached the endpoint of VA/SCD (16/60) had significantly higher mean R2I2 than those that did not (1.11±0.09 vs. 0.84±0.04, p=0.003). Patients were partitioned into "high risk" and "low risk" groups on the basis of the predefined R2I2 value of 1.03 and a Kaplan Meier curve constructed (FIG. 19A). Patients with R2I2≥1.03 had a significantly higher rate of VA/SCD than patients with R2I2<1.03 (p<0.0001). A receiver operating characteristic analysis found that R2I2 significantly discriminated between those experiencing VA/SCD and those without during follow-up (area under curve of 0.770, FIG. 19B). A Piecewise Poisson model of R2I2 found that patients with R2I2≥1.03 had a VA/SCD incidence rate ratio 7.5 times that of patients with R2I2<1.03 (p=0.004). A second Piecewise Poisson model that included R2I2, programmed electrical stimulation result, left ventricular ejection fraction and QRS duration showed that the R2I2≥1.03 was an independent predictor of VA/SCD with a incidence rate ratio of 6.5 (p=0.008).

An R2I2 cut-off value of 1.03 gave sensitivity 63%, specificity 82%, positive predictive value 56%, negative predictive value 86%.

Peak Electrocardiogram Restitution Gradient (PERG—Also May be Referred to as PERS; Peak Electrocardiogram Restitution Slope)

Peak ECG restitution gradient was significantly higher in patients experiencing VA/SCD than in patients not (1.35 [0.60]vs.1.08[0.52], p=0.014). A Piecewise Poisson model of PERG found that patients with PERG≥1.21 had a VA/SCD incidence rate ratio 4.1 times that of patients with PERG<1.21 (p=0.017). A second Piecewise Poisson model that included PERG, programmed electrical stimulation result, left ventricular ejection fraction and QRS duration showed that PERG≥1.21 was an independent predictor of VA/SCD with a incidence rate ratio of 4.9 (p=0.006).

Spearman rank correlation analysis found minimal positive correlation between peak ECG restitution gradient and R2I2 (r=0.290, p=0.025, FIG. 20). Piecewise Poisson models that included R2I2≥1.03 and PERG≥1.21 showed that R2I2≥1.03 (IRR 5.8, p=0.001) and PERG≥1.21 (IRR 3.7, p=0.027) were independent predictors of VA/SCD. A Kaplan Meier curve was constructed for patients partitioned by both R2I2≥1.03 and PERG≥1.21 and showed significant separation (p<0.0001, FIG. 21). A Piecewise Poisson model found that patients with R2I2≥1.03 and PERG≥1.21 had a VA/SCD incidence rate ratio 21.6 times that of patients with R2I2<1.03 and PERG<1.21 (p<0.0001). Combining R2I2≥1.03 and PERG≥1.21 gave sensitivity 50%, specificity 95%, positive predictive value 80%, negative predictive value 84%. 15

DISCUSSION

This blinded study successfully replicated the findings of a retrospective study of R2I2 that used the same technique developed for R2I2 analysis and the same endpoints. (11) The relative risk of VA/SCD in patients with high R2I2 values was 6.5 that of low risk R2I2 patients. PERG was also found to be significantly steeper in patients experiencing VA/SCD than in those not; the relative risk of VA/SCD in patients with PERG≥1.21 was 4.9 times that of PERG<1.21 patients. Importantly both R2I2 and PERG were independent of the programmed electrical stimulation result, left ventricular ejection fraction and QRS duration suggesting that they may add value to existing markers of VA/SCD risk. Furthermore, in a combined model the strong association with VA/SCD was retained for both R2I2 (IRR 5.8) and PERG (IRR 3.7). In patients positive for both R2I2≥1.03 and PERG≥1.21 the relative risk of VA/SCD was 21.6 times that of patients negative for both. The positive predictive value for VA/SCD in patients with both R2I2≥1.03 and PERG≥1.21 is 80% with a specificity of 95%.

The strength of R2I2 and PERG is in their identification of a very high risk group, even amongst ICM patients in whom an ICD is currently recommended by guidelines. Using the previously determined R2I2 cut-off of 1.03, the rate of VA/SCD in those above this threshold was 63% at 18 months; for 17 patients with R2I2≥1.03 and PERG≥1.21 the rate of VA/SCD was 82% at 18 months. This is considerably higher than patients recruited to the MADIT II and SCD-heft trials who had a rate of appropriate ICD therapy of less than 10% per year. (25) Individuals with high R2I2 and/or PERG therefore represent a particular but substantial group amongst those receiving ICDs where further research should be focused to try and reduce risk. In addition, the findings raise the possibility that R2I2 and PERG might retain sufficient positive predictive value for clinical utility when applied to lower risk populations such as patients with LVEF over 35% for whom risk stratification is currently very limited. (26) This requires further evaluation.

CONCLUSIONS

R2I2 and PERG are independent biomarkers of VA/SCD risk in patients with ICM. In combination, in this study, they provided an 80% positive predictive value and 95% specificity.

The invention claimed is:

1. A method for assessing the electrical function of a heart, the method comprising the steps of:
providing an ECG, the ECG having a plurality of leads;
determining, for each lead of the plurality of leads, at more than one time point, an output value corresponding to an action potential duration;
determining, for each lead of the plurality of leads, at the more than one time points, an output value corresponding to a diastolic interval;
determining a restitution curve for each of the plurality of leads based on the output value corresponding to the action potential and the output value corresponding to the diastolic interval at the more than one time points;
determining a gradient of the restitution curve for each of the plurality of leads at a first time point;
combining the gradients determined for each lead; or
identifying the steepest gradient amongst the gradients taken for each lead at the first time point,
wherein a steeper gradient indicates a higher likelihood to progress to cardiac failure.

2. The method of claim 1, wherein the indication of the higher likelihood to progress to cardiac failure is an assessment of need for implantation of an implantable cardioverter defibrillator or administration of an anti-arrhythmic agent.

3. The method of claim 1, wherein the action potential duration is measured as a QT or a JT interval, and wherein the diastolic interval is measured as the TQ interval.

4. The method of claim 1, wherein the gradient is a numerical gradient.

5. The method of claim 1, wherein the action potential duration and the diastolic interval are each measured in the same manner for each of the plurality of leads.

6. The method of claim 1, further comprising:
assessing the differences between the restitution curves for each of the plurality of leads, wherein the greater the differences between the restitution curves for each lead indicates a higher risk that the heart is abnormal; and
assessing the cardiac function of the heart, determining the need for implantation of an implantable cardioverter defibrillator or the need for administration of an anti-arrhythmic agent based on the gradient of the restitution curve and the differences between the restitution curves.

7. The method of claim 1, wherein the plurality of leads comprises two or more selected from the group consisting of limb leads, chest leads, posterior leads, anterior leads, lateral leads, or inferior leads.

8. An apparatus for assessing the function of the heart, the apparatus comprising:
an ECG having a plurality of leads; and
a computer in communication with the ECG, wherein the computer performs the steps of:
determining, for each lead of the plurality of leads, at more than one time point, an output value corresponding to an action potential duration;
determining, for each lead of the plurality of leads, at the more than one time points, an output value corresponding to a diastolic interval;
determining a based on the output value corresponding to the action potential and the output value corresponding to the diastolic interval at the more than one time points;
determining a gradient of the restitution curve for each of the plurality of leads at a first time point;
combining the gradients determined for each lead; or
identifying the steepest gradient amongst the gradients taken for each lead at the first time point,
wherein a steeper gradient indicates a higher likelihood to progress to cardiac failure.

9. The apparatus of claim 8, wherein the action potential duration is measured as a QT or a JT interval, and wherein the diastolic interval is measured as the TQ interval.

10. The apparatus of claim 8, the gradient is a numerical gradient.

11. The apparatus of claim 8, wherein the action potential duration and the diastolic interval are each measured in the same manner for each of the plurality of leads.

12. The apparatus of claim 8, further comprising:
assessing the differences between the restitution curves for each of the plurality of leads, wherein the greater the differences between the restitution curves for each lead indicates a higher risk that the heart is abnormal; and
assessing the cardiac function of the heart, determining the need for implantation of an implantable cardioverter defibrillator or the need for administration of an anti-arrhythmic agent based on the gradient of the restitution curve and the differences between the restitution curves.

13. One or more non-transitory computer storage media having computer-executable instructions embodied thereon that, when executed, perform a method for assessing the electrical function of a heart, the method comprising:
communicating with an ECG, the ECG having a plurality of leads;
receiving, at more than one time point, an output value corresponding to an action potential duration from each lead of the plurality of leads;
receiving, at the more than one time points, an output value corresponding to a diastolic interval from each lead of the plurality of leads;
determining a restitution curve based on the output value corresponding to the action potential and the output value corresponding to the diastolic interval, for each lead of the plurality leads at the more than one time points;
determining a gradient of the restitution curve for each of the plurality of leads at a first time point;
combining the gradients determined for each lead; or
identifying the steepest gradient amongst the gradients taken for each lead at the first time point,
wherein a steeper gradient indicates a higher likelihood to progress to cardiac failure.

14. The media of claim 13, wherein the action potential duration and the diastolic interval are each measured in the same manner for each lead.

15. The media of claim 13, wherein the action potential duration is measured as a QT or a JT interval, and wherein the diastolic interval is measured as the TQ interval.

16. The media of claim 13, wherein the gradient is a numerical gradient.

17. The media of claim 13, wherein the action potential duration and the diastolic interval are each measured in the same manner for each of the plurality of leads.

18. The media of claim 13, wherein the indication of the higher likelihood to progress to cardiac failure is an assessment of need for implantation of an implantable cardioverter defibrillator or administration of an anti-arrhythmic agent.

19. The media of claim 13, further comprising:
assessing the differences between the restitution curves for each of the plurality of leads, wherein the greater the differences between the restitution curves for each lead indicates a higher risk that the heart is abnormal; and
assessing the cardiac function of the heart, determining the need for implantation of an implantable cardioverter defibrillator or the need for administration of an anti-arrhythmic agent based on the gradient of the restitution curve and the differences between the restitution curves.

20. The media of claim 13, wherein the leads comprise at least one selected from the group consisting of limb leads, chest leads, posterior leads, anterior leads, lateral leads, inferior leads.

21. The method of claim 1, wherein the method further comprises calculating an average gradient across the leads after combining the gradients determined for each lead.

22. The apparatus of claim 8, wherein the computer further performs the step of calculating an average gradient cross the leads after combining the gradients determined for each lead.

23. The one or more non-transitory computer storage media of claim 13, wherein the method further comprises calculating an average gradient across the leads after combining the gradients determined for each lead.

* * * * *